US012728086B2

(12) United States Patent
Nelp et al.

(10) Patent No.: US 12,728,086 B2
(45) Date of Patent: Sep. 8, 2026

(54) SUNSCREENS DERIVED FROM KYNURENINES AND OTHER UV-ABSORBING OXIDIZED AMINO ACIDS BOUND TO PEPTIDES OR POLYMERS

(71) Applicants: The Trustees of Princeton University, Princeton, NJ (US); THE UNIVERSITY OF UTAH, Salt Lake City, UT (US)

(72) Inventors: Micah T. Nelp, Montrose, CO (US); Anthony P. Young, Salt Lake City, UT (US); John T. Groves, Princeton, NJ (US)

(73) Assignees: The Trustees of Princeton University, Princeton, NJ (US); The University of Utah, Salt Lake City, UT (US)

( * ) Notice: Subject to any disclaimer, the term of this patent is extended or adjusted under 35 U.S.C. 154(b) by 338 days.

(21) Appl. No.: 18/282,372

(22) PCT Filed: Mar. 16, 2022

(86) PCT No.: PCT/US2022/020578

§ 371 (c)(1),
(2) Date: Sep. 15, 2023

(87) PCT Pub. No.: WO2022/197819

PCT Pub. Date: Sep. 22, 2022

(65) Prior Publication Data

US 2024/0307285 A1 Sep. 19, 2024

Related U.S. Application Data

(60) Provisional application No. 63/277,026, filed on Nov. 8, 2021, provisional application No. 63/215,661, filed (Continued)

(51) Int. Cl.
*A61K 8/44* (2006.01)
*A61K 8/64* (2006.01)
*A61Q 17/04* (2006.01)

(52) U.S. Cl.
CPC ................ *A61K 8/445* (2013.01); *A61K 8/64* (2013.01); *A61Q 17/04* (2013.01)

(58) Field of Classification Search
None
See application file for complete search history.

(56) References Cited

U.S. PATENT DOCUMENTS

2003/0153727 A1 8/2003 Kenten et al.
2004/0042072 A1 * 3/2004 Gallas .................... G02B 1/041 359/356

(Continued)

FOREIGN PATENT DOCUMENTS

EP 1038516 A1 9/2000

OTHER PUBLICATIONS

Sherin, S.S., et al., Photophysics and Photochemistry of the UV Filter Kynurenine Covalently Attached to Amino Acids and to a Model Protein, J. Phys. Chem., 114 (2010) pp. 11909-11919. (Year: 2010).*

(Continued)

*Primary Examiner* — Dominic Lazaro
(74) *Attorney, Agent, or Firm* — Meagher Emanuel Laks Goldberg & Liao LLP

(57) ABSTRACT

The present disclosure provides compositions of matter comprising a polymer or peptide bound to an oxidized amino acid or an analog thereof. The present disclosure also provides packaging materials, consumer products, and cosmetic products comprising the compositions of matter disclosed herein.

15 Claims, 8 Drawing Sheets

Related U.S. Application Data on Jun. 28, 2021, provisional application No. 63/162,267, filed on Mar. 17, 2021.

(56) References Cited

U.S. PATENT DOCUMENTS

| | | | | |
|---|---|---|---|---|
| 2006/0194719 | A1 | 8/2006 | Ebbehoj et al. | |
| 2011/0201947 | A1 | 8/2011 | HaZen et al. | |
| 2012/0189627 | A1* | 7/2012 | Heavner | A61P 3/10 424/134.1 |
| 2020/0032062 | A1* | 1/2020 | Wallin | B33Y 10/00 |

OTHER PUBLICATIONS

Hidalgo, F.J & Zamora, R., Amino Acid Degradations Produced by Lipid Oxidation Products, Crit. Rev. Food Sci. Nutr., 56 (2016) pp. 1242-1252. (Year: 2016).*

European Search Report corresponding PCT Application No. PCT/US2022020578, dated Nov. 26, 2024.

Sherin Peter S et al: "Photophysics and photochemistry of the UV filter kynurenine covalently attached to amino acids and to a model protein.", The Journal of Physical Chemistry. Sep. 16, 2010, vol. 114, No. 36, Sep. 16, 2010.

Stutchbury G.M. et al: "The Modification of Proteins by 3-Hydroxykynurenine", Experimental Eye Research, vol. 57, Aug. 1993.

Todorovski Toni et al: "Synthesis of peptides containing 5-hydroxytryptophan, oxindolylalanine, N-formylkynurenine and kynurenine", Journal of Peptide Science, vol. 17, No. 4, Jan. 19, 2011.

International Search Report & Written Opinion for corresponding PCT Application No. PCT/US2022/020578, dated Jun. 17, 2022.

* cited by examiner

SUNSCREENS DERIVED FROM KYNURENINES AND OTHER UV-ABSORBING OXIDIZED AMINO ACIDS BOUND TO PEPTIDES OR POLYMERS

GOVERNMENT SUPPORT

This invention was made with government support under CHE-1900048 awarded by the National Science Foundation (NSF). The government has certain rights in the invention.

BACKGROUND

Materials that absorb ultraviolet (UV) light are useful for a variety of purposes, such as in sunscreens to prevent skin damage or disease and in packaging materials to prevent degradation of the packaged contents. However, many UV light-absorbing compounds or materials are harmful to humans and/or the environment. The safety of a number of currently used active ingredients of sunscreens, such as para-aminobenzoic acid, trolamine salicylate, have been recently called into question, while other potential active ingredients require more information before being considered safe and effective, including cinoxate, dioxybenzone, ensulizole, homosalate, meradimate, octinoxate, octisalate, octocrylene, padimate O, sulisobenzone, oxybenzone, and avobenzone. These ingredients, as well as UV light-absorbing compounds or materials commonly used in packaging materials, may also be dangerous to animals and the environment. Thus, there exists a need to develop non-toxic UV light-absorbing compounds or materials for use in sunscreens, packaging materials, and other products.

SUMMARY OF THE INVENTION

The present disclosure provides compositions of matter comprising a polymer or peptide bound to an oxidized amino acid or an analog thereof.

In some aspects, the oxidized amino acid or an analog thereof is an oxidation product of an amino acid selected from the group consisting of tryptophan, tyrosine, phenylalanine, methionine, cysteine, and histidine.

In some aspects, the oxidized amino acid or an analog thereof is an oxidation product of tryptophan.

In some aspects, the oxidation product of tryptophan is kynurenine or an analog thereof.

In some aspects, the kynurenine or an analog thereof is L-kynurenine, D-kynurenine, N-formyl-L-kynurenine, N-formyl-D-kynurenine, 3-hydroxy-L-kynurenine, 3-hydroxy-D-kynurenine, (E)-4-(2-aminophenyl)-4-oxobut-2-enoic acid, (Z)-4-(2-aminophenyl)-4-oxobut-2-enoic acid, or a combination thereof.

In some aspects, the molecular weight of the composition of matter is from about 100 Da to about 100,000 Da.

In some aspects, the molecular weight is from about 100 Da to about 1,000 Da.

In some aspects, the molecular weight is from about 1,000 Da to about 20,000 Da.

In some aspects, the molecular weight is from about 5,000 Da to about 25,000 Da.

In some aspects, the oxidized amino acid or an analog thereof is derived from a food-grade material selected from the group consisting of soy, oat, whey, pea, hemp, and corn.

In some aspects, the oxidized amino acid or an analog thereof is synthetically derived.

In some aspects, the peptide is synthetic or naturally derived.

In some aspects, the peptide is naturally derived from a food-grade material selected from the group consisting of soy, oat, whey, pea, hemp, and corn.

In some aspects, the peptide comprises histidine, lysine, cysteine, or a combination thereof.

In some aspects, the polymer is synthetic or naturally derived.

In some aspects, the polymer is a naturally derived polymer selected from the group consisting of chitosan, poly-lysine and polyamines.

In some aspects, the polymer is a synthetic polymer selected from the group consisting of poly(meth)acrylates, polymethyl(meth)acrylates, polyamides, polyurethanes, polyvinylacrylates, polyesters, poly(meth)acrylic acid esters, polyvinylesters, polylactic acid esters, polyhydroxyalkanoates, polyhydroxybutyrate, polyhydroxybutyric acid, and copolymers or combinations thereof.

In some aspects, the peptide or polymer has a nucleophilic group.

In some aspects, the composition of matter is formed through the addition of a nucleophilic residue on the peptide or polymer to the oxidized amino acid or an analog thereof.

In some aspects, the oxidized amino acid or an analog thereof is (E)-4-(2-aminophenyl)-4-oxobut-2-enoic acid, (Z)-4-(2-aminophenyl)-4-oxobut-2-enoic acid, or a combination thereof.

In some aspects, the nucleophilic residue on the peptide or polymer adds to the 2-carbon of (E)-4-(2-aminophenyl)-4-oxobut-2-enoic acid or (Z)-4-(2-aminophenyl)-4-oxobut-2-enoic acid.

In some aspects, the composition of matter is formed through the addition of an aromatic amine of a first kynurenine or an analog thereof to a second kynurenine or an analog thereof.

In some aspects, the second kynurenine or an analog thereof is (E)-4-(2-aminophenyl)-4-oxobut-2-enoic acid, (Z)-4-(2-aminophenyl)-4-oxobut-2-enoic acid, or a combination thereof.

In some aspects, the aromatic amine of the first kynurenine or an analog thereof adds to the 2-carbon of (E)-4-(2-aminophenyl)-4-oxobut-2-enoic acid or (Z)-4-(2-aminophenyl)-4-oxobut-2-enoic acid.

In some aspects, a peptide bound to kynurenine or an analog thereof is purified using reversible covalent addition of nucleophilic immobilized resins to ketone groups of the kynurenine or an analog thereof.

In some aspects, a peptide bound to N-formyl kynurenine is purified using reversible covalent addition of nucleophilic immobilized resins to the electrophilic groups of N-formyl kynurenine.

In some aspects, the composition of matter is formed via an amide bond between an amine of the polymer and the carboxylate of kynurenine or an analog thereof.

In some aspects, the composition of matter is formed via an amide bond between a carboxylic acid of the polymer and an amine of kynurenine or an analog thereof.

The present disclosure also provides packaging materials comprising the compositions of matter disclosed herein.

In some aspects, the composition of matter is a coating applied to the surface of the packaging material.

In some aspects, the composition of matter is an additive dispersed throughout the packaging material.

In some aspects, the packaging material is selected from the group consisting of thermoplastic polymer, polyvinyl chloride (PVC), polyethylene, polyethylene terephthalate (PET), low density polyethylene (LDPE), high density polyethylene (HDPE), polystyrene (PS), plastic wrap, aluminum, aluminum foil, laminates and metallized films, tin-free steel, tin-coated steel, ceramics, and glass.

In some aspects, the thickness of the packaging material is from about 0.1 mm to about 50 mm.

In some aspects, the composition of matter provides UVB and UVA protection centered at from about 350 nm to about 370 nm.

In some aspects, the composition of matter provides about 12 to 24 months stability to a packaged product.

In some aspects, the packaging material is manufactured in the form of a container, a bottle, a cap, or a flexible outer film.

In some aspects, the packaging material comprises from about 0.1 wt % to about 10 wt % of the composition of matter, based on the total weight of the packaging material.

In some aspects, the packaging material is transparent or translucent.

In some aspects, the packaging material is used for food packaging, cosmetics, or medical products.

In some aspects, the packaging material is a food packaging material.

In some aspects, the packaging material comprises a cross-linking agent.

In some aspects, the cross-linking agent is selected from the group consisting of tetraethylorthosilicate, malonic acid, glutaric acid, adipic acid, citric acid, butanetetracarboxylic acid and maleic acid, and combinations thereof.

The present disclosure also provides consumer products comprising the compositions of matter disclosed herein.

The present disclosure also provides cosmetic products comprising the compositions of matter disclosed herein.

In some aspects, the product is a sunscreen characterized by photostability and nonradiative relaxation that provides UV-A and UV-B protection.

In some aspects, the product is selected from the group consisting of lotions, light ointments, oils, gels, emulsions, mousses, aerosols, sticks and powders.

In some aspects, the product further comprises a product vehicle.

In some aspects, the product vehicle is selected from water, ethanol, or oil, or a combination thereof.

In some aspects, the product provides UVB and UVA protection centered at from about 350 nm to about 370 nm.

In some aspects, the product further comprises one or more of an oil component, a moisturizing agent, a surfactant, and a carrier.

In some aspects, the carrier is a water-in-oil emulsion, an oil, an aqueous-based lotion or gel, or an anhydrous gel.

In some aspects, the product comprises from about 0.1 wt % to about 25 wt % of the composition of matter.

In some aspects, the product further comprises one or more thickening agents, film forming agents, surfactants, skin conditioning agents, or a combination thereof.

In some aspects, the product has a pH of from about 5 to about 9.

In some aspects, the product has a pH of from about 7.5 to about 8.5.

The present disclosure also provides methods of making the products described herein, wherein the method comprises the steps of (a) adding deionized water to a vessel; (b) heating the water; (c) adding a carrier oil and an anionic surfactant to the vessel; (d) slowly adding the composition of matter to the vessel and heating and mixing the resultant composition; and (e) optionally, adjusting the pH of said composition.

DETAILED DESCRIPTION

Definitions

Figure 1:
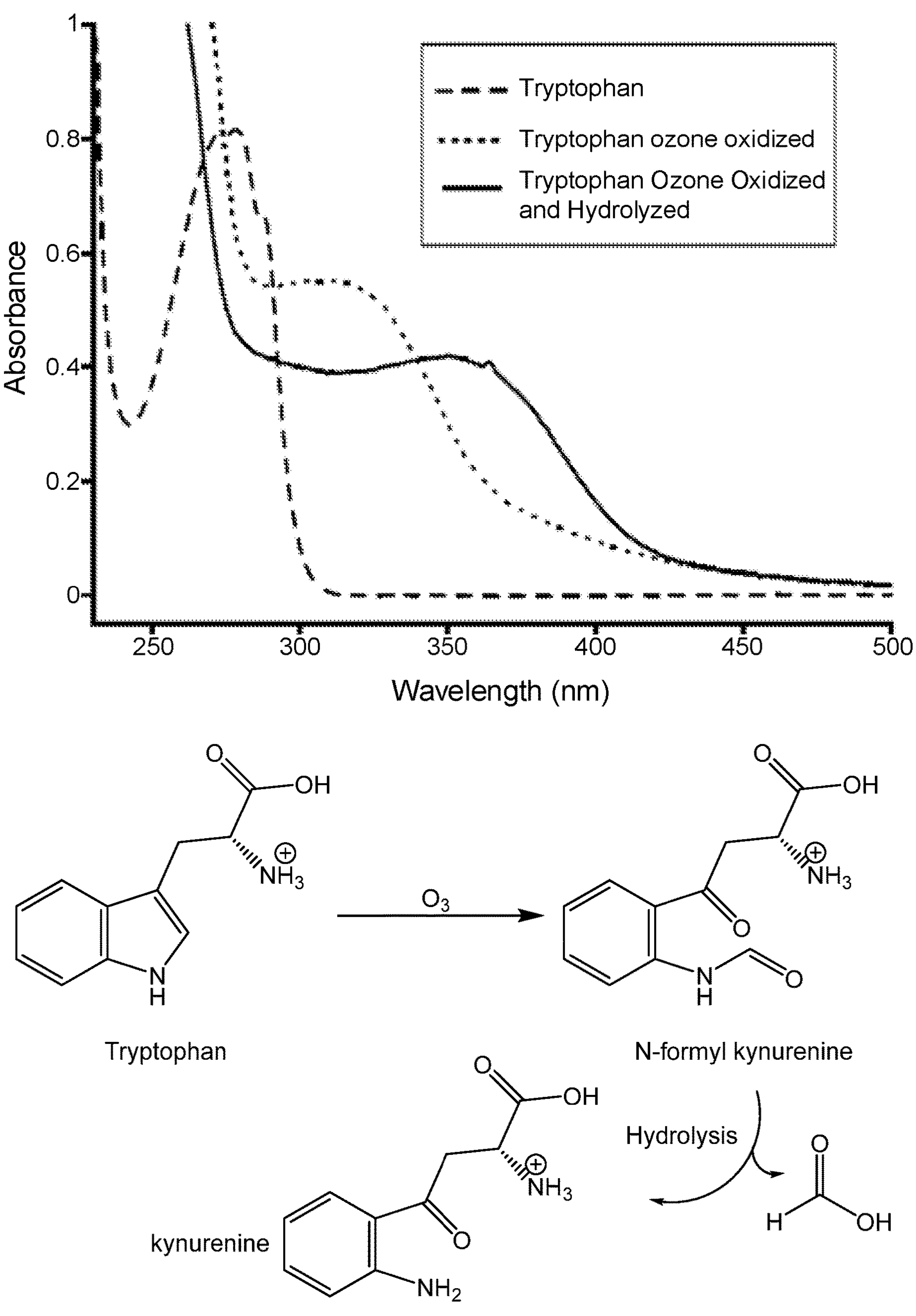
FIG. 1 is a line graph (top) showing the UV spectra of L-tryptophan, N-formyl kynurenine after exposure to ozone, and kynurenine after hydrolysis; and a reaction scheme (bottom) showing tryptophan being converted to N-formyl kynurenine then kynurenine and analogs thereof upon oxidation with ozone.

Unless defined otherwise, all technical and scientific terms used herein have the same meaning as commonly understood by one of ordinary skill in the art to which this disclosure belongs. In case of conflict, the present application including the definitions will control. Unless otherwise required by context, singular terms shall include pluralities and plural terms shall include the singular. All publications, patents and other references mentioned herein are incorporated by reference in their entireties for all purposes as if each individual publication or patent application were specifically and individually indicated to be incorporated by reference.

Although methods and materials similar or equivalent to those described herein can be used in practice or testing of the present disclosure, suitable methods and materials are described below. The materials, methods and examples are illustrative only and are not intended to be limiting. Other features and advantages of the disclosure will be apparent from the detailed description and from the claims.

In order to further define this disclosure, the following terms and definitions are provided.

The singular forms "a," "an" and "the" include plural referents unless the context clearly dictates otherwise. The terms "a" (or "an"), as well as the terms "one or more," and "at least one" can be used interchangeably herein. In certain aspects, the term "a" or "an" means "single." In other aspects, the term "a" or "an" includes "two or more" or "multiple."

The term "about" is used herein to mean approximately, roughly, around, or in the regions of When the term "about" is used in conjunction with a numerical range, it modifies that range by extending the boundaries above and below the numerical values set forth. In general, the term "about" is used herein to modify a numerical value above and below the stated value by a variance of 10 percent, up or down (higher or lower).

The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Overview

As detailed herein and in the Figures, disclosed herein are sunscreens derived from kynurenines and other UV-absorbing oxidized amino acids, or analogs thereof, bound to peptides or polymers.

In some examples, the disclosed approach comprises new compositions of matter such as with non-natural peptides or polymers bearing kynurenines and other UV-absorbing amino acids, or analogs thereof.

In other examples, the disclosed approach comprises a new use for some naturally occurring polypeptides containing oxidized tryptophan, tyrosine, and phenylalanine residues, though the complete oxidation of all useful residues (tryptophan, tyrosine, and phenylalanine) is unlikely to occur in untreated food and cosmetic grade peptides, and so this example too would include a novel composition of matter being the natural peptides treated with oxidants to effect a more complete conversion to the UV-protective derivatives.

The disclosed approach could be used as a UV-protective component of sunscreens. Because an embodiment is of naturally occurring derivatives of food-grade peptides and proteins, the disclosed approach provides UV-protective, non-toxic, biodegradable topical sunscreens, additives in packaging, and food preservatives.

Oxidized amino acids, or analogs thereof, derived from protein sources exhibit desirable UV-protective absorption and energy dissipation that will be useful as active sunscreen ingredients. Because oxidized amino acids, or analogs thereof, are naturally derived and are readily catabolized by living organisms, they are ideal sunscreens to replace the current state of the art xenobiotic sunscreens that are ecologically damaging and pose potential threats to human health.

Tryptophan can be oxidized by reactive oxygen species to 2, 4, 5, 6, or 7, hydroxy-tryptophan, all of which have redshifted absorbance relative to parent tryptophan, giving protection in the 290-305 nm UVB region. Another set of oxidation tryptophan side chain products includes kynurenine, N-formyl kynurenine, and 3-hydroxykynurenine (kynurenines) which are capable of absorbing a broad range of UVB and UVA. The corresponding monomeric amino acids are also naturally derived from tryptophan catabolism in what is known as the kynurenine pathway, leading to multiple downstream products such as the essential cofactor nicotinamide adenine dinucleotide.

Other genetically encoded, common amino acids in food grade protein sources may also be oxidized to UVB-absorbing derivatives including phenylalanine and tyrosine residues, which can form quinones and dityrosyl crosslinks. These will be referred to hereafter as "other oxidized amino acids." There are methods to favor oxidation of tryptophan to the most desirable kynurenines, or analogs thereof, such as by reaction at lower pH. Other amino acids are also likely to become oxidatively modified including methionine, cysteine, and histidine, the products of which can be selectively reduced (disulfides to thiols) or do not inhibit the UV-protective effects of the desired kynurenine modifications.

In one embodiment, the disclosed approach entails a sunscreen utilizing oxidized amino acid residues derived from ribosomally translated and post-translationally oxidized tryptophan, tyrosine, and phenylalanine residues in proteins and smaller peptide fragments from food grade sources (such as those derived from pea, soy, whey, etc.). Multiple methods are available to effect these oxidations including treating the tryptophan- tyrosine- and phenylalanine-containing peptides with singlet oxygen, ozone, Fenton chemistry, chlorine dioxide, peroxynitrite, photoexcitation, or electrochemical oxidation. The primary example of this type of UV-protection derives from peptides containing tryptophan, tyrosine, and phenylalanine (and to a lesser extent methionine, cysteine, and histidine) that when treated with ozone, produce a range of products exhibiting a broad absorbance of UVB and UVA centered at 327 nm without breakage of the peptide bonds.

Kynurenine and other oxidized amino acid derivative-containing polymers offer a distinct advantage over other currently approved active ingredients in topical sunscreens because they are readily prepared in the form of large molecules (>500 Da) that prevent or greatly diminish absorption through the skin into deeper tissue and blood. An FDA clinical trial recently reported that six active ingredients in common sunscreens were absorbed into blood after routine usage, and conclude "had plasma concentrations that surpassed the FDA threshold for potentially waiving some of the additional safety studies for sunscreens." A proposed FDA rule (86 FR 6204) would classify two of the current active ingredients of sunscreens as no longer to be considered safe (para-aminobenzoic acid and trolamine salicylate) while twelve others would require more information before being considered safe and effective (cinoxate, dioxybenzone, ensulizole, homosalate, meradimate, octinoxate, octisalate, octocrylene, padimate O, sulisobenzone, oxybenzone, and avobenzone). There is evidence these organic sunscreens may also cause considerable ecological damage, especially to aquatic systems. Under this proposed rule, only two currently approved active ingredients, inorganic zinc oxide and titanium oxide, would be considered safe and effective up to 25%, though even these have shown concerning effects on aquatic ecosystems. For these reasons, biocompatible, effective kynurenine, or an analog thereof, and other oxidized amino acid, or an analog thereof, based polymer sunscreens will be of significant utility.

Sunscreen molecules by their nature absorb UV radiation and can thus act as oxygen photosensitizers producing reactive singlet oxygen. Once absorbed, these sunscreen molecules actually increase the amount of reactive oxygen species when exposed to sunlight. One of the advantages of peptides bearing kynurenine, or an analog thereof, is that they do not absorb through the skin (when greater than 500

Da), and so they prevent this self-inflicted photosensitization and oxidative damage that other small molecule sunscreens can cause. Kynurenine, or an analog thereof, bound to proteins can still likely produce singlet oxygen, but the average distance singlet oxygen travels, ~150 nm, is far shorter than even the thinnest areas of upper skin layer, the stratum corneum that varies from ~10 μm (cheek) to 50 μm (palm). Kynurenine or analog thereof bearing peptides are thus unlikely to produce reactive oxygen species deep into the nucleated layers of skin; They are even less likely to form because of the still effective UV screening of the peptides at the skin surface.

As large molecules, kynurenine-containing and other oxidized amino acid based polymers may adhere to skin much better than currently approved small molecule sunscreens. Proteins and other large polymers have the potential to interact with keratin on the human epidermis through multiple hydrophobic, ionic, and even covalent binding, allowing for enhanced UV-protection over small molecule alternatives that could more readily be washed away by sweat, water, and clothing/towels. Indeed, some peptides have been described that specifically adhere to skin and hair which may be covalently attached to these polymers bearing kynurenines, or analogs thereof, and other oxidized amino acids, or analogs thereof.

The disclosed approach also comprises an environmentally friendly alternative to organic UV-filters coated onto plastics and glass.

A further use may derive from the bioactivity of free kynurenine amino acids, or analogs thereof, that are immunomodulatory compounds. Polymers that bear kynurenines, or analogs thereof, and proteins specifically would work well for this purpose, wherein upon hydrolysis in the body they could act as a slower-release form of immunomodulatory kynurenines, or analogs thereof, than treatment with the free amino acid counterparts.

The disclosed approach provides a biologically derived sunscreen made with components that are biodegradable and which are readily metabolized by humans and other organisms. Kynurenines, or analogs thereof, (and oxidized tyrosine and phenylalanine residues) differ from currently approved sunscreen active components that are ecologically damaging and which can accumulate in human blood plasma with known xenoestrogenic and other potential negative effects.

Unlike current sunscreen dyes that absorb through skin and accumulate in blood plasma, kynurenine, or an analog thereof, and other oxidized amino acid bearing polymers will improve safety by minimizing the absorption through skin by anchoring the active UV-protective kynurenine, or an analog thereof, residues to peptides that are sufficiently large to prevent diffusion through the upper layers of the skin. These kynurenine, or an analog thereof, bearing peptides may also be designed or selected to adhere to proteins on the skin's surface, reducing loss through water and sweat and further preventing absorption through the skin.

By using kynurenine, or an analog thereof, peptides derived from known food grade material, the likelihood of allergic reactions is diminished, and consumers can be aware of the risk before use based upon which food source is used, such as oat, pea, soy, whey peptides etc.

In one form, kynurenine- (and oxidized tyrosine and phenylalanine-) based sunscreens can be conveniently obtained by treating aqueous protein or peptides derived from enzymatic hydrolysis of proteins (such as food grade cosmetic moisturizing peptides of pea, oat, soy, or whey peptides) with oxidants that break the indole 2,3 bond of constituent tryptophan residues producing N-formylkynurenine residues that spontaneously hydrolyze to kynurenine and formaldehyde. Other modifications include oxidation of tyrosine residues to dityrosines and tyrosine-oxygen-tyrosine crosslinks and oxidation of both tyrosine and phenylalanine to their DOPA derivatives. Such oxidants include ozone, singlet oxygen, or hydrogen peroxide and metal catalysts (heme, iron salts, etc.). To remove formaldehyde and catalysts/sensitizers if used, the kynurenine containing-peptides can be dialyzed with a semipermeable membrane using an appropriate molecular mass cutoff (>1 kDa).

Synthetically-derived proteins/peptides offer the ability to produce designed sequences that could be engineered to include desired qualities such as enhanced adherence, increased concentration of kynurenines, or analogs thereof, per molecule for better UV-absorption, and lack of potentially cross-reactive residues (such as cysteine and tyrosine).

One such source could be synthetically derived peptides from solid phase synthesis. This allows for designed peptides to be utilized including those containing non-proteogenic amino acids and other components.

Another source of proteins and peptides with designed sequences is heterologous expression in common hosts such as *E. coli, S. cerevisiae*, or *S. pichia*. Though this generally limits the polymer to UV-absorbing variants of only genetically encoded amino acids, this method offers a cost-effective input of microbial food sources and extensive possible means of purification of product peptide.

A prototype of oxidized amino acid-bearing peptides from enzymatic hydrolysate of pea protein was made. The pea peptone was oxidized with ozone to produce oxidized derivatives of the peptide-bound tryptophan, tyrosine, and phenylalanine residues resulting in increased absorbance from 300-350 nm. More particularly, peptides derived from enzymatic hydrolysis of pea protein (Sigma, 16974) were oxidized in 50 mM sodium phosphate buffer at room temperature using ozone bubbled through the solution (A2Z Ozone Inc., MP1000). The formation of kynurenine, or an analog thereof, products was monitored by UV-visible spectroscopy which showed an increase in the absorbance between 300-400 nm, where the free amino acids of N-formyl kynurenine, kynurenine, and 3-hydroxy kynurenine, dityrosine, O-linked dityrosine, and 3,4-dihydroxyphenylalanine also absorb. Free L-tryptophan was treated similarly and showed strong broad-spectrum absorbance from 300 to 400 nm.

More particularly, to confirm oxidation occurs with tryptophan residues, 1 mM free L-tryptophan (Sigma, T0254) was similarly reacted with ozone in distilled water and showed high reactivity as shown by UV-visible spectroscopy with increasing absorbance over time between 300-400 nm that likely derives from absorbance of product of N-formyl kynurenine. Using peptides enriched in tryptophan residues would likely improve upon the UVB (300-330 nm) and UVA (330 to 400 nm) absorption by increasing the relative concentration of strongly absorbing kynurenine products of tryptophan residue oxidation.

FIG. 1 shows the UV-absorbance of pea protein hydrolysate peptides treated with ozone, along with a comparison with the UV-visible spectrum of products of the same reaction on free tryptophan treated similarly.

The disclosed approach can be used as an alternative to organic dyes and inorganic nanoparticles in sunscreens formulated as oils, lotions, creams, gels, butters, pastes, sticks, ointments, sprays, etc. It has the advantage of being biologically derived, even from food-grade sources. As large polymers, these sunscreens are likely to adhere to surface skin proteins better than current dyes, and they will not absorb into tissue and enter circulation in the body. Unlike many compounds approved for use as topical sunscreens by the FDA, protein, peptides, and kynurenines, or analogs thereof, and other oxidized amino acids, or analogs thereof, are not xenobiotics that pose a health risk if consumed or absorbed, and they will be far less ecologically damaging to sensitive aquatic life threatened by accumulation of current sunscreen dyes from swimmers.

The commercial paths for these products are, inter alia, as active ingredients in topical sunscreens, UV-protective packaging, and as UV-protective food preservatives. Companies producing cosmetics, sunscreens, or UV-protective filters on plastics or glass, among others, will find value in the disclosed approach. Kynurenine, or an analog thereof, peptides specifically may also find medicinal use as a slow-release form of their immunomodulatory component residues.

Naturally occurring and abundant polymers may contain residues other than tryptophan that may also be oxidized along with tryptophan, tyrosine, and phenylalanine depending upon which method of oxidation is used, such as methionine, cysteine, and histidine. These oxidized residues exist naturally in peptides and proteins, and so ozone, singlet oxygen, and photo-oxidation products are unlikely to be toxic or interfere with the UV-absorption of kynurenines, or analogs thereof, and other desired oxidized amino acids, or analogs thereof.

Covalent crosslinking of peptides that contain cysteine and tyrosine residues may occur when they are oxidized to disulfides and tyrosine adducts. The resultant cystines can be treated with reductants back to free cysteinyl thiols, such as with the small molecule dithiothreitol that will not react with or interfere with the kynurenine, or an analog thereof, residues and can be dialyzed away from the final product. To avoid crosslinking of tyrosine and histidine residues, methods exist to minimize these side reactions such as by adjusting pH of the reaction solution (e.g. lowering the pH of the reaction solution to well below the pKa of tyrosine and histidine).

Compositions of Matter

The present disclosure provides compositions of matter comprising a polymer or peptide bound to an oxidized amino acid or an analog thereof.

As used herein, the term "oxidized amino acid" refers to any oxidation product of an amino acid, and further oxidation products or metabolites thereof. Amino acids can be oxidized by any oxidation method known in the art, including but not limited to, singlet oxygen, ozone, Fenton chemistry, chlorine dioxide, peroxynitrite, photoexcitation, or electrochemical oxidation. Further oxidation products or metabolites thereof include oxidized amino acids that have been deaminated by natural catabolic processes or by synthetic processes known in the art.

In some aspects, the oxidized amino acid is an oxidation product of tyrosine, phenylalanine, methionine, cysteine, or histidine. In some aspects, the oxidized amino acid is an oxidation product of tryptophan. In some aspects, the oxidation product of tryptophan is kynurenine or an analog thereof.

As used herein, the term "kynurenine or an analog thereof" refers to kynurenine, L-kynurenine, D-kynurenine, compounds from which kynurenine is derived, and compounds derived from kynurenine via oxidative or catabolic processes. In some aspects, "kynurenine or an analog thereof" refers to N-formyl-L-kynurenine, N-formyl-D-kynurenine, 3-hydroxy-L-kynurenine, 3-hydroxy-D-kynurenine, (E)-4-(2-aminophenyl)-4-oxobut-2-enoic acid, (Z)-4-(2-aminophenyl)-4-oxobut-2-enoic acid, or a combination thereof.

In some aspects, the molecular weight of the composition of matter is from about 100 Da to about 500 Da, from about 100 Da to about 1,000 Da, from about 100 Da to about 5,000 Da, from about 100 Da to about 10,000 Da, from about 100 Da to about 25,000 Da, from about 100 Da to about 50,000 Da, from about 100 Da to about 100,000 Da, from about 500 Da to about 1,000 Da, from about 500 Da to about 5,000 Da, from about 500 Da to about 10,000 Da, from about 500 Da to about 25,000 Da, from about 500 Da to about 50,000 Da, from about 500 Da to about 100,000 Da, In some aspects, the molecular weight of the composition of matter is about 100 Da, about 250 Da, about 500 Da, about 750 Da, about 1,000 Da, about 2,500 Da, about 5,000 Da, about 7,500 Da, about 10,000 Da, about 25,000 Da, about 50,000 Da, about 75,000 Da, or about 100,000 Da.

In some aspects, the oxidized amino acid or an analog thereof is derived from a food-grade material. Food-grade materials include, but are not limited to, soy, oat, whey, pea, hemp, and corn.

In some aspects, the oxidized amino acid or an analog thereof is synthetically derived.

In some aspects, the composition of matter comprises a peptide. In some aspects, the peptide is naturally derived. Peptides may be naturally derived from any natural source. In some aspects, the natural source is a food grade-material.

In some aspects, the peptide is synthetically derived. Synthetic peptides may be prepared using solid-phase peptide synthesis or by other synthetic techniques known in the art.

In some aspects, the peptide comprises histidine, lysine, cysteine, or a combination thereof.

In some aspects, the composition of matter comprises a polymer. In some aspects, the polymer is naturally derived. Naturally derived polymers include, but are not limited to, chitosan, poly-lysine, polyamines, and combinations thereof.

In some aspects, the polymer is a synthetic polymer. Synthetic polymers include, but are not limited to, poly(meth)acrylates, polymethyl(meth)acrylates, polyamides, polyurethanes, polyvinylacrylates, polyesters, poly(meth)acrylic acid esters, polyvinylesters, polylactic acid esters, polyhydroxyalkanoates, polyhydroxybutyrate, polyhydroxybutyric acid, and copolymers or combinations thereof.

In some aspects, the peptide or polymer comprises a nucleophilic group. In some aspects, the nucleophilic group is an amino group.

In some aspects, the composition of matter is formed when the nucleophilic group of the polymer or peptide forms a bond with an oxidized amino acid, or an analog thereof. In some aspects, the oxidized amino acid, or an analog thereof, is (E)-4-(2-aminophenyl)-4-oxobut-2-enoic acid, (Z)-4-(2-aminophenyl)-4-oxobut-2-enoic acid, or a combination thereof. In some aspects, the nucleophilic group of the polymer or peptide adds to the 2-carbon of the (E)-4-(2-aminophenyl)-4-oxobut-2-enoic acid or (Z)-4-(2-aminophenyl)-4-oxobut-2-enoic acid via a Michael addition reaction.

In some aspects, the composition of matter is formed through the addition of an aromatic amine of a first kynurenine or an analog thereof to a second kynurenine or an analog thereof. In some aspects, the second kynurenine or an analog thereof is (E)-4-(2-aminophenyl)-4-oxobut-2-enoic acid, (Z)-4-(2-aminophenyl)-4-oxobut-2-enoic acid, or a combination thereof. In some aspects, the aromatic amine of the first kynurenine or an analog thereof adds to the 2-carbon of (E)-4-(2-aminophenyl)-4-oxobut-2-enoic acid or (Z)-4-(2-aminophenyl)-4-oxobut-2-enoic acid.

In some aspects, the composition of matter is formed via an amide bond between an amine of the polymer and the carboxylate of kynurenine or an analog thereof. In some aspects, the composition of matter is formed via an amide bond between a carboxylic acid of the polymer and an amine of kynurenine or an analog thereof. Amide bond formation can be accomplished through standard coupling techniques known in the art.

The present disclosure also provides methods of purifying the compositions of matter described herein. In some aspects, a composition of matter comprising a peptide bound to kynurenine or an analog thereof is purified using reversible covalent addition of nucleophilic immobilized resins to ketone groups of the kynurenine or an analog thereof.

In some aspects, a composition of matter comprising a peptide bound to N-formyl kynurenine is purified using reversible covalent addition of nucleophilic immobilized resins to the electrophilic groups of N-formyl kynurenine.

Packaging Materials

The present disclosure also provides packaging materials comprising the compositions of matter disclosed herein.

In some aspects, the composition of matter is a coating applied to the surface of the packaging material. In some aspects, the coating is applied by spraying a solution comprising the composition of matter onto the surface of the packaging material.

In some aspects, the composition of matter is an additive dispersed throughout the packaging material. In some aspects, the composition of matter is a dry powder that may be added to a mixture or solution, wherein said mixture or solution is used to form the packaging material. In some aspects, the mixture or solution comprises one or more polymers.

In some aspects, the packaging material comprises a thermoplastic polymer, polyvinyl chloride (PVC), polyethylene, polyethylene terephthalate (PET), low density polyethylene (LDPE), high density polyethylene (HDPE), polystyrene (PS), plastic wrap, aluminum, aluminum foil, laminates and metallized films, tin-free steel, tin-coated steel, ceramics, glass, or combinations thereof.

The term "thermoplastic polymer" is intended to encompass any synthetic polymeric material that exhibits a modification in physical state from solid to liquid upon exposure to sufficiently high temperatures. Non-limiting examples of thermoplastic polymers include polyolefins (i.e., polypropylene, polyethylene, and the like), polyester (i.e., polyethylene terephthalate, and the like), polyamides (i.e., nylon-1,1, nylon-1,2, nylon-6 or nylon-6,6), polystyrenes, polyurethanes, polycarbonates, polyvinyl halides (i.e., polyvinyl chloride and polyvinvyl difluoride, as merely examples), and the like.

In some aspects, the packaging material comprises one or more cross-linking agents. Non-limiting examples of cross-linking agents include tetraethylorthosilicate, malonic acid, glutaric acid, adipic acid, citric acid, butanetetracarboxylic acid and maleic acid.

In some aspects, the packaging material comprises from about 0.1 wt % to about 10 wt % of the composition of matter. In some aspects, the packaging material comprises from about 0.1 wt % to about 0.5 wt %, from about 0.1 wt % to about 1 wt %, from about 0.1 wt % to about 1.5 wt %, from about 0.1 wt % to about 2.5 wt %, from about 0.1 wt % to about 5 wt %, from about 0.1 wt % to about 7.5 wt %, from about 0.5 wt % to about 1 wt %, from about 0.5 wt % to about 1.5 wt %, from about 0.5 wt % to about 2.5 wt %, from about 0.5 wt % to about 5 wt %, from about 0.5 wt % to about 7.5 wt %, from about 0.5 wt % to about 10 wt %, from about 1 wt % to about 1.5 wt %, from about 1 wt % to about 2.5 wt %, from about 1 wt % to about 5 wt %, from about 1 wt % to about 7.5 wt %, from about 1 wt % to about 10 wt %, from about 1.5 wt % to about 2.5 wt %, from about 1.5 wt % to about 5 wt %, from about 1.5 wt % to about 7.5 wt %, from about 1.5 wt % to about 10 wt %, from about 2.5 wt % to about 5 wt %, from about 2.5 wt % to about 7.5 wt %, from about 2.5 wt % to about 10 wt %, from about 5 wt % to about 7.5 wt %, from about 5 wt % to about 10 wt %, or from about 7.5 wt % to about 10 wt % of the composition of matter. In some aspects, the packaging material comprises from about 10 wt % to about 25 wt %, from about 12.5 wt % to about 25 wt %, from about 15 wt % to about 25 wt %, from about 17.5 wt % to about 25 wt %, from about 20 wt % to about 25 wt %, from about 10 wt % to about 20 wt %, from about 12.5 wt % to about 20 wt %, from about 15 wt % to about 20 wt %, from about 17.5 wt % to about 20 wt %, from about 10 wt % to about 17.5 wt %, from about 12.5 wt % to about 17.5 wt %, from about 15 wt % to about 17.5 wt %, from about 10 wt % to about 15 wt %, from about 12.5 wt % to about 15 wt %, or from about 10 wt % to about 12.5 wt % of the composition of matter. In some aspects, the packaging material comprises from about 1 wt % to about 12.5 wt %, from about 1 wt % to about 15 wt %, from about 1 wt % to about 17.5 wt %, from about 1 wt % to about 20 wt %, from about 1 wt % to about 25 wt %, from about 5 wt % to about 12.5 wt %, from about 5 wt % to about 15 wt %, from about 5 wt % to about 17.5 wt %, from about 5 wt % to about 20 wt %, from about 5 wt % to about 25 wt %, from about 7.5 wt % to about 12.5 wt %, from about 7.5 wt % to about 15 wt %, from about 7.5 wt % to about 17.5 wt %, from about 7.5 wt % to about 20 wt %, from about 7.5 wt % to about 25 wt % of the composition of matter.

In some aspects, the packaging material comprises about 1 wt % of the composition of matter. In some aspects, the packaging material comprises about 0.1 wt %, about 0.5 wt %, about 1.5 wt %, about 2.5 wt %, about 5 wt %, about 7.5 wt %, or about 10 wt % of the composition of matter. In some aspects, the packaging material comprises about 12.5 wt %, about 15 wt %, about 17.5 wt %, about 20 wt %, or about 25 wt % of the composition of matter.

In some aspects, the thickness of the packaging material is from about 0.01 mm to about 0.1 mm, from about 0.01 mm to about 0.5 mm, from about 0.01 mm to about 1 mm, from about 0.01 mm to about 2.5 mm, from about 0.01 mm to about 5 mm, from about 0.01 mm to about 10 mm, from about 0.1 mm to about 0.5 mm, from about 0.1 mm to about 1 mm, from about 0.1 mm to about 2.5 mm, from about 0.1 mm to about 5 mm, from about 0.1 mm to about 10 mm, from about 0.5 mm to about 1 mm, from about 0.5 mm to about 2.5 mm, from about 0.5 mm to about 5 mm, from about 0.5 mm to about 10 mm, from about 1 mm to about 2.5 mm, from about 1 mm to about 5 mm, from about 1 mm to about 10 mm, from about 2.5 mm to about 5 mm, from about 2.5 mm to about 10 mm, or from about 5 mm to about 10 mm.

In some aspects, the composition of matter provides UVA and UVB protection centered at from about 350 nm to about 370 nm. In some aspects, the protection is centered at from about 300 nm to about 320 nm, from about 310 nm to about 330 nm, from about 320 nm to about 340 nm, from about 330 nm to about 350 nm, from about 340 nm to about 360 nm, from about 360 nm to about 380 nm, from about 370 nm to about 390 nm, from about 380 nm to about 400 nm, or from about 390 nm to about 410 nm.

In some aspects, UV transmission through the packaging material is at most 10% at each wavelength under 390 nm. In some aspects, UV transmission through the packaging material is at most 20%, at most 25%, at most 30%, at most 35%, at most 40%, at most 45%, at most 50%, at most 55%, at most 60%, at most 65%, or at most 70% at each wavelength under 390 nm.

In some aspects, the packaging material is transparent or translucent. In some aspects, the packaging material is very low in color. In some aspects, the packaging material does not exhibit a b* value (indicating a degree of yellowing in this instance) above 2.5 on the CieLab scale.

In some aspects, the compositions of matter disclosed herein exhibit low migratory levels when incorporated into a packaging material comprising a polymeric material. In some aspects, the compositions of matter exhibit low migratory levels due to the high hydrophilicity of the compositions of matter. In some aspects, the compositions of matter exhibit low migratory levels due to the high molecular weight of the compositions of matter.

In some aspects, the packaging material is manufactured in the form of a bottle, a storage container, a sheet, a film, a fiber, a plaque, a hose, a tube, or a syringe. Included within this list would be polyester, polystyrene and other like clear resinous materials in sheet form which are present within windows for strength and resiliency functions. In such an instance, the low-color UV absorbers of this invention would provide or contribute to excellent UV protection for contents with target packaging articles (such as bottles, containers, and the like) or persons located indoors (such as within houses, buildings, cars, and the like, comprising windows with such additives included therein).

In some aspects, the packaging material is used for food packaging, cosmetics, or medical products.

Ultraviolet absorbers, such as the compositions of matter disclosed herein, are typically added to such compositions during the injection molding (or other type of molding, such as blow molding), thereof, including, and without limitation, by mixing the liquid absorber with resin pellets and melting the entire coated pellets, or through a masterbatch melting step while the resin and absorber are pre-mixed and incorporated together in pellet form. Such plastics include, again without limitation, polyolefins, polyesters, polyamides, polyurethanes, polycarbonates, and other resins, such as those disclosed within U.S. Pat. Nos. 4,640,690 4,507,407, herein incorporated by reference. Generally, such plastics, including the UV absorber additive, are formed through any number of various extrusion techniques, such as those disclosed in the aforementioned U.S. patents.

Consumer and Cosmetic Products

The present disclosure also provides consumer and cosmetic products comprising the compositions of matter disclosed herein.

In some aspects, the product is a sunscreen. In some aspects, the sunscreen is characterized by photostability and nonradiative relaxation that provides UV-A and UV-B protection.

In some aspects, the product is a lotion, a light ointment, an oil, a gel, an emulsion, a mousse, an aerosol, a stick or a powder.

In some aspects, the product further comprises a product vehicle. Non-limiting examples of product vehicles include water, ethanol, oil, and combinations thereof.

In some aspects, the product provides UVA and UVB protection centered at from about 350 nm to about 370 nm. In some aspects, the protection is centered at from about 300 nm to about 320 nm, from about 310 nm to about 330 nm, from about 320 nm to about 340 nm, from about 330 nm to about 350 nm, from about 340 nm to about 360 nm, from about 360 nm to about 380 nm, from about 370 nm to about 390 nm, from about 380 nm to about 400 nm, or from about 390 nm to about 410 nm.

In some aspects, UV transmission through the product is at most 10% at each wavelength under 390 nm. In some aspects, UV transmission through the packaging material is at most 20%, at most 25%, at most 30%, at most 35%, at most 40%, at most 45%, at most 50%, at most 55%, at most 60%, at most 65%, or at most 70% at each wavelength under 390 nm.

In some aspects, the product further comprises an oil component. Non-limiting examples of oil components include hydrocarbon oils, higher fatty acids, higher alcohols, synthetic esters, silicone oils, liquid fats and oils, solid fats and oils, and waxes.

Examples of the hydrocarbon oils include liquid petrolatum, ozocerite, squalane, pristane, paraffin, ceresin, squalene, petrolatum, and microcrystalline wax.

Examples of the higher fatty acids include lauric acid, myristic acid, palmitic acid, stearic acid, behenic acid, oleic acid, undecylenic acid, tall oil, isostearic acid, linolic acid, linoleic acid, eicosapentaenoic acid (EPA), and docosahexaenoic acid (DHA).

Examples of the higher alcohols include straight chain alcohols (for example, lauryl alcohol, cetyl alcohol, stearyl alcohol, behenyl alcohol, myristyl alcohol, oleyl alcohol, and cetostearyl alcohol) and branched chain ethyl alcohols (for example, mono stearyl glyceryl ether (batyl alcohol), 2-decyltetradecynol, lanolin alcohol, cholesterol, phytosterol, hexyl dodecanol, isostearyl alcohol, and octyl dodecanol).

Examples of the synthetic ester oils include octyl octanoate, nonyl nonanoate, cetyl octanoate, isopropyl myristate, octyl dodecyl myristate, isopropyl palmitate, butyl stearate, hexyl laurate, myristyl myristate, decyl oleate, dimethyl hexyl decyl octanoate, cetyl lactate, myristyl lactate, lanolin acetate, isocetyl stearate, isocetyl isostearate, cholesteryl 12-hydroxystearate, di-2-ethylene glycol ethylhexanoate, dipentaerythritol fatty acid ester, N-alkylene glycol monoisostearate, neopentyl glycol dicaprate, tripropylene glycol pivalate, diisostearyl malate, glyceryl di-2-heptylundecanoate, glyceryl diisostearate, trimethylolpropane tri-2-ethyl hexanoate, trimethylolpropane triisostearate, tetra-2-pentaerythritol ethylhexanoate, glyceryl tri-2-ethylhexanoate, glyceryl trioctanoate, glyceryl triisopalmitate, trimethylolpropane triisostearate, cetyl 2-ethyl hexanoate 2-ethylhexyl palmitate, glyceryl trimyristate, tri-2-heptyl undecanoic acid glyceride, methyl castor oil fatty acid, oleyl oleate, aceto glyceride, 2-heptylundecyl palmitate, diisobutyl adipate, 2-octyldodecyl N-lauroyl-L-glutamate, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate, and triethyl citrate.

Examples of the silicone oils include chain polysiloxanes (for example, dimethylpolysiloxane, methylphenyl polysiloxane, and diphenyl polysiloxane); ring polysiloxanes (for example, octamethylcyclotetrasiloxane, decamethyl cyclopentasiloxane, and dodecamethyl cyclohexasiloxane), silicone resins having a three-dimensional network structure, silicone rubbers, various modified polysiloxanes (amino-modified polysiloxane, polyether-modified polysiloxane, alkyl-modified polysiloxane, and fluorine-modified polysiloxane), and acryl silicones.

Examples of the liquid fats and oils include avocado oil, tsubaki oil, turtle fatty acid, macademia nut oil, corn oil, mink oil, olive oil, rapeseed oil, egg yolk oil, sesame oil, persic oil, wheat germ oil, sasanqua oil, castor oil, linseed oil, safflower oil, cotton seed oil, perilla oil, soybean oil, peanut oil, tea seed oil, Japanese nutmeg oil, rice bran oil, Chinese gimlet oil, Japanese gimlet oil, jojoba oil, germ oil, and triglycerides.

Examples of the solid fats and oils include cacao butter, coconut oil, horse fat, hydrogenated coconut oil, palm oil, beef tallow, mutton tallow, hydrogenated beef tallow, palm kernel oil, lard, beef bone fat, Japanese core wax nucleus oil, hydrogenated oil, neatsfoot oil, Japanese core wax, and hydrogenated castor oil.

Examples of the waxes include beeswax, candelilla wax, cotton wax, carnauba wax, bayberry wax, tree wax, whale wax, montan wax, bran wax, lanolin, kapok wax, lanolin acetate, liquid lanolin, sugar cane wax, lanolin fatty acid isopropyl ester, hexyl laurate, reduced lanolin, jojoba wax, hard lanolin, shellac wax, POE lanolin alcohol ether, POE lanolin alcohol acetate, POE cholesterol ether, lanolin fatty acid polyethylene glycol, and POE hydrogenated lanolin ethyl alcohol ether.

In some aspects, the product further comprises one or more moisturizers. Moisturizers include, but are not limited to, $C_1$-$C_{20}$ alkyl esters of fatty acids, $C_{10}$-$C_{22}$ fatty acids (i.e., stearyl, palmityl, lauryl, myristyl acids), $C_{10}$-$C_{22}$ fatty alcohols (stearyl, palmityl, lauryl, myristyl, oleyl alcohols), and $C_{10}$-$C_{22}$ fatty alcohol ethers, $C_{16}$-$C_{22}$ alkanoic triglycerides (e.g., sunflower seed oil), sterols such as cholesterol and soy sterol, silicones (e.g., dimethicone), petroleum jelly, and mineral oils.

In some aspects, the product further comprises one or more emollients. Suitable emollients include those agents known for softening the skin which may be selected from hydrocarbons, fatty acids, fatty alcohols and esters. Petrolatum is a common hydrocarbon type of emollient conditioning agent. Other agents that may be employed include alkyl benzoate, mineral oil, polyolefins such as polydecene, and paraffins, such as isohexadecane. Fatty acids and alcohols used typically have from about 10 to 30 carbon atoms. Oily ester emollients may be those selected from one or more of the following: triglyceride esters, acetoglyceride esters, ethoxylated glycerides, alkyl esters of fatty acids, ether esters, polyhydric alcohol esters and wax esters. Additional emollients or hydrophobic agents include $C_{12}$-$C_{15}$ alkyl benzoate, dioctyladipate, octyl stearate, octyidodecanol, hexyl laurate, octyldodecyl neopentanoate, cyclomethicone, dicapryl ether, dimethicone, phenyl trimethicone, isopropyl myristate, capriylic/capric triglycerides, propylene glycol dicaprylate/dicaprate and decyl oleate, cyclomethicones and other silicone derivatives. Additional emollients include cetearyl alcohol, isoamyl laurate, glyceryl stearate citrate, glyceryl caprylate, caprylic/capric triglyceride, and cetearyl isononanoate.

In some aspects, the product further comprises a surfactant. The surfactant may be anionic, cationic, ampholytic, or non-ionic.

Non-limiting examples of anionic surfactants include fatty acid soaps (for example, sodium laurate and sodium palmitate); higher alkyl sulfuric acid ester salts (for example, sodium lauryl sulfate and potassium lauryl sulfate); alkyl ether sulfuric acid ester salts (for example, POE-triethanolamine lauryl sulfate and sodium POE-lauryl sulfate); N-acyl sarcosinic acids (for example, sodium lauroyl sarcosinate); higher fatty acid amide sulfonic acid salts (for example, sodium N-myristoyl N-methyl taurate, Sodium N-cocoyl-N-methyl taurate, and Sodium jauroylmethyl taurate); phosphoric ester salts (for example, sodium POE-oleyl ether phosphate and POE stearyl ether phosphoric acid); sulfosuccinates (for example sodium di-2-ethylhexylsulfosuccinate, sodium monolauroyl monoethanol amide polyoxyethylene sulfosuccinate, and sodium lauryl polypropylene glycol sulfosuccinate); alkyl benzene sulfonates (for example, sodium linear dodecyl benzene sulfonate, triethanolamine linear dodecyl benzene sulfonate, and linear dodecyl benzene sulfonic acid); higher fatty acid ester sulfates (for example, hydrogenated coconut oil aliphatic acid glyceryl sodium sulfate); N-acyl glutamates (for example, mono sodium N-lauroylglutamate, disodium N-stearoylglutamate, and sodium N-myristoyl-L-glutamate); sulfated oils (for example, turkey red oil); POE-alkyl ether carboxylic acid; POE-alkyl aryl ether carboxylate; α-olefin sulfonate; higher fatty acid ester sulfonates; sec-alcohol sulfates; higher fatty acid alkyl amide sulfates; sodium lauroyl monoethanolamine succinates; ditriethanolamine N-palmitoylaspartate; and sodium caseinate.

Non-limiting examples of cationic surfactants include quaternary ammonium salts such as cetyltrimethylammonium chloride, stearyltrimethylammonium chloride, benenyltrimethylammonium chloride, behenyldimethylhydroxyethylammonium chloride, stearyldimethylbenzylammonium chloride, and cetyltrimethylammonium methylsulfate. Other examples include amide amine compounds such as stearic diethylaminoethylamide, stearic dimethylaminoethylamide, palmitic diethylaminoethylamide, palmitic dimethylaminoethylamide, myristic diethylaminoethylamide, myristic dimethylaminoethylamide, behenic diethylaminoethylamide, behenic dimethylaminoethylamide, stearic diethylaminopropylamide, stearic dimethylaminopropylamide, palmitic diethylaminopropylamide, palmitic dimethylaminopropylamide, myristic diethylaminopropylamide, myristic dimethylaminopropylamide, behenic diethylaminopropylamide, and behenic dimethylaminopropylamide.

Non-limiting examples of ampholytic surfactants include imidazoline type ampholytic surfactants (for example, 2-undecyl-1-hydroxyethyl-1-carboxymethyl-4,5-dihydro-2-imidazolium sodium salt and 1-[2-(carboxymethoxy)ethyl]-1-(carboxymethyl)-4,5-dihydro-2-norcocoalkylimidazolium hydroxide disodium salt) and betaine type surfactants (for example, 2-heptadecyl-N-carboxymethyl-N-hydroxyethyl imidazolinium betaine, lauryldimethylarninoacetic acid betaine, alkyl betaine, amide betaine, and sulfobetaine).

Non-limiting examples of non-ionic surfactants include glycerol fatty acid esters, ethylene oxide derivatives of glyceryl fatty acid esters, polyglycerol fatty acid esters, propylene glycol fatty acid esters, ethylene oxide derivatives of propylene glycol fatty acid esters, polyethylene glycol fatty acid esters, polyethylene glycol alkyl ethers, polyethylene glycol alkyl phenyl ethers, polyethylene glycol castor oil derivatives, polyethylene glycol hydrogenated castor oil derivatives, polyether-modified silicone and polyglycerin-modified silicone. Further examples include POE-sorbitan fatty acid esters (for example, POE-sorbitan monooleate, POE-sorbitan monostearate, POE-sorbitan monooleate, and POE-sorbitan tetraoleate); POE sorbitol fatty acid esters (for example, POE sorbitol monolaurate, POE-sorbitol monooleate, POE-sorbitolpentaoleate, and POE-sorbitol monostearate); POE-glyceryl fatty acid esters (for example, POE-monooleates such as POE-glyceryl monostearate, POE-glyceryl monoisostearate, and POE glycerin glyceryl triisostearate); POE-fatty acid esters (for example, POE-distearate, POE-monodioleate, and ethylene glycol distearate); POE-alkylethers (for example, POE-lauryl ether, POE-oleyl ether, POE-stearyl ether, POE-behenyl ether, POE 2-octyl dodecyl ether, and POE-cholestanol ether); pluaronics (for example, pluaronic); POE•POP-alkylethers (for example, POE•POP-cetyl ether, POE•POP2-decyl tetradecyl ether, POE•POP-monobutyl ether, POE•POP-lanolin hydrate, and POE•POP glycerin glyceryl ether); tetra POE•tetra POP-ethylenediamino condensates (for example, tetronic); POE-castor oil hydrogenated castor oil derivatives (for example, POE-castor oil, POE-hydrogenated castor oil, POE-hydrogenated castor oil monoisostearate, POE-hydrogenated castor oil triisostearate, POE-hydrogenated castor oil monopyroglutamic monoisostearic diester, and POE-hydrogenated castor oil maleic acid); POE-beeswax•lanolin derivatives (for example, POE-sorbitol beeswax); alkanol amides (for example, palm oil fatty acid diethanol amide, laurate monoethanolamide, and fatty acid isopropanol amide); POE-propylene glycol fatty acid esters; POE-alkylamines; POE-fatty acid amides; sucrose fatty acid esters; alkyl ethoxydimethylamine oxides; and trioleyl phosphoric acid.

In some aspects, the product further comprises a carrier. In some aspects, the carrier is a water-in-oil emulsion, an oil, an aqueous-based lotion or gel, or an anhydrous gel.

In some aspects, the product comprises from about 0.1 wt % to about 2.5 wt % of the composition of matter. In some aspects, the product comprises from about 0.1 wt % to about 0.5 wt %, from about 0.1 wt % to about 1 wt %, from about 0.1 wt % to about 1.5 wt %, from about 0.1 wt % to about 2 wt %, from about 0.1 wt % to about 2.5 wt %, from about 0.5 wt % to about 1 wt %, from about 0.5 wt % to about 1.5 wt %, from about 0.5 wt % to about 2 wt %, from about 0.5 wt % to about 2.5 wt %, from about 1 wt % to about 1.5 wt %, from about 1 wt % to about 2 wt %, from about 1 wt % to about 2.5 wt %, from about 1.5 wt % to about 2 wt %, from about 1.5 wt % to about 2.5 wt %, or from about 2 wt % to about 2.5 wt % of the composition of matter.

In some aspects, the product comprises about 1 wt % of the composition of matter. In some aspects, the product comprises about 0.1 wt %, about 0.5 wt %, about 1.5 wt %, about 2 wt %, or about 2.5 wt % of the composition of matter.

In some aspects, the product further comprises one or more thickening agents, film forming agents, skin conditioning agents, or a combination thereof.

In some aspect, the product has a pH of from about 5 to about 9. In some aspects, the product has a pH of from about 6.5 to about 7.5, from about 6 to about 7, from about 7 to about 8, or from about 7.5 to about 8.5.

The present disclosure also provides methods of making the products disclosed herein. In some aspects, the method comprises the steps of (a) adding deionized water to a vessel; (b) heating the water; (c) adding a carrier oil and an anionic surfactant to the vessel; (d) slowly adding the composition of matter to the vessel and heating and mixing the resultant composition; and (e) optionally, adjusting the pH of said composition.

The following examples are illustrative and do not limit the scope of the claimed aspects.

EXAMPLES

Example 1

Oxidation of Free L-tryptophan

Free L-tryptophan dissolved in deionized water was treated with ozone to produce the dioxygenated product, N-formyl kynurenine, resulting in increased absorbance from 300-350 nm (FIG. 1). This oxidation product was then heated to 100° C. for 1 hour to effect hydrolysis of the formyl group, producing free kynurenine that absorbs well at 350 to 370 nm (FIG. 1). Using peptides enriched in tryptophan residues would likely improve upon the UVB (300-330 nm) and UVA (330 to 400 nm) absorption by increasing the relative concentration of strongly absorbing kynurenine products of tryptophan residue oxidation.

Example 2

Oxidation of Model Lysine-Tryptophan-Lysine (KWK) Tripeptide

Figure 2:
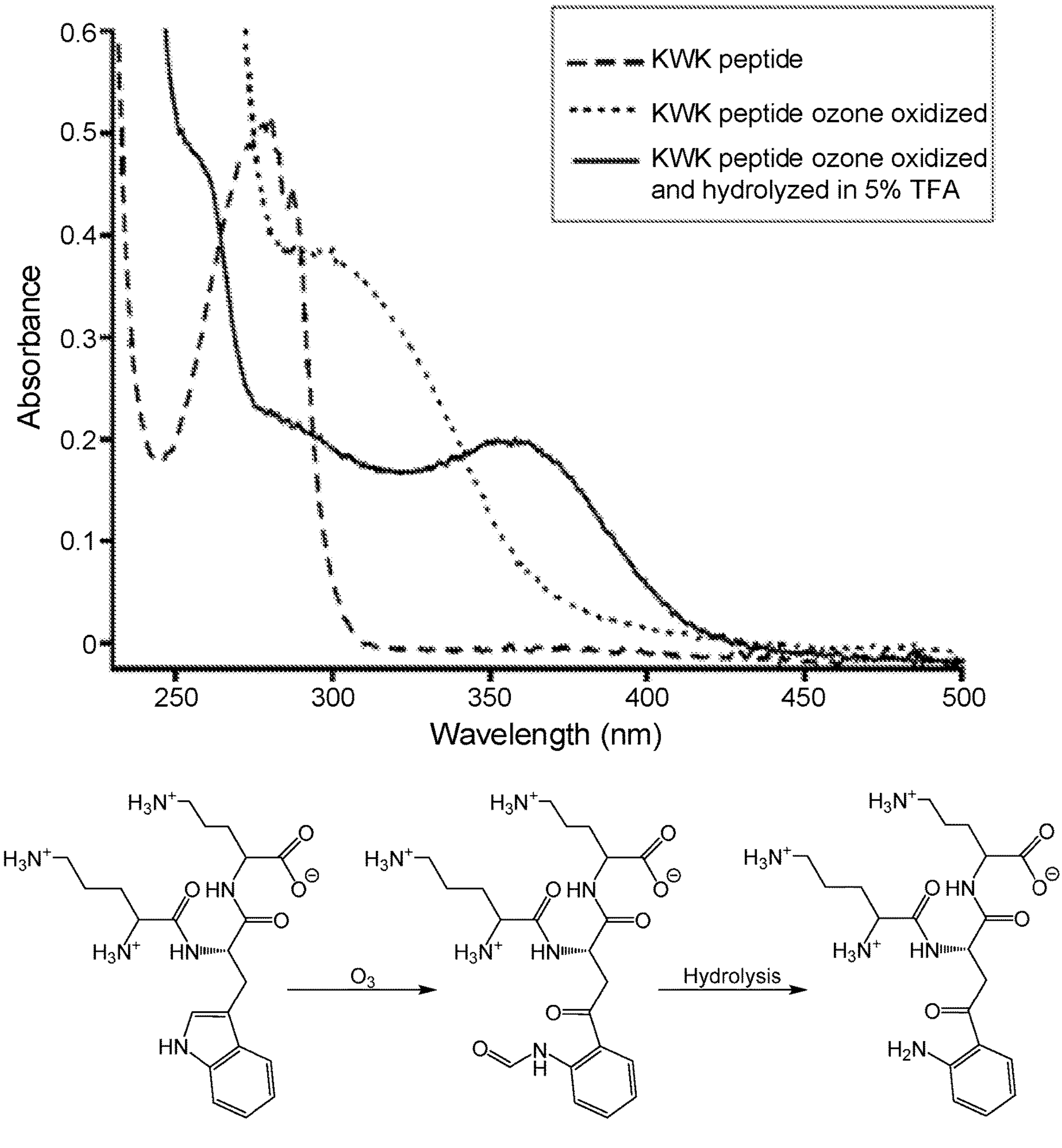
FIG. 2 is line graph (top) showing the UV spectra of the KWK tripeptide before modification, after treatment with ozone for 4 h, and after further treatment with 5% trifluoroacetic acid (TFA) for 30 min or after further being boiled for 1 h (top); and a reaction scheme (bottom) showing the reaction of ozone with KWK and further hydrolysis.

A prototype was produced using a peptide of defined sequence, generated from solid phase synthesis. This lysine-tryptophan-lysine (KWK) tripeptide was treated with ozone for 4 h in aqueous solution to produce an oxidized N-formyl kynurenine-bound peptide. The UV spectrum of this peptide is shown in FIG. 2 (top). Further treatment with acid gave the hydrolyzed lysine-kynurenine-lysine tripepetide. The UV spectrum of this product is also shown in FIG. 2 (top). The product identity was confirmed using LC-MS.

Example 3

Oxidation of Soy and Pea Peptides

Figure 3:
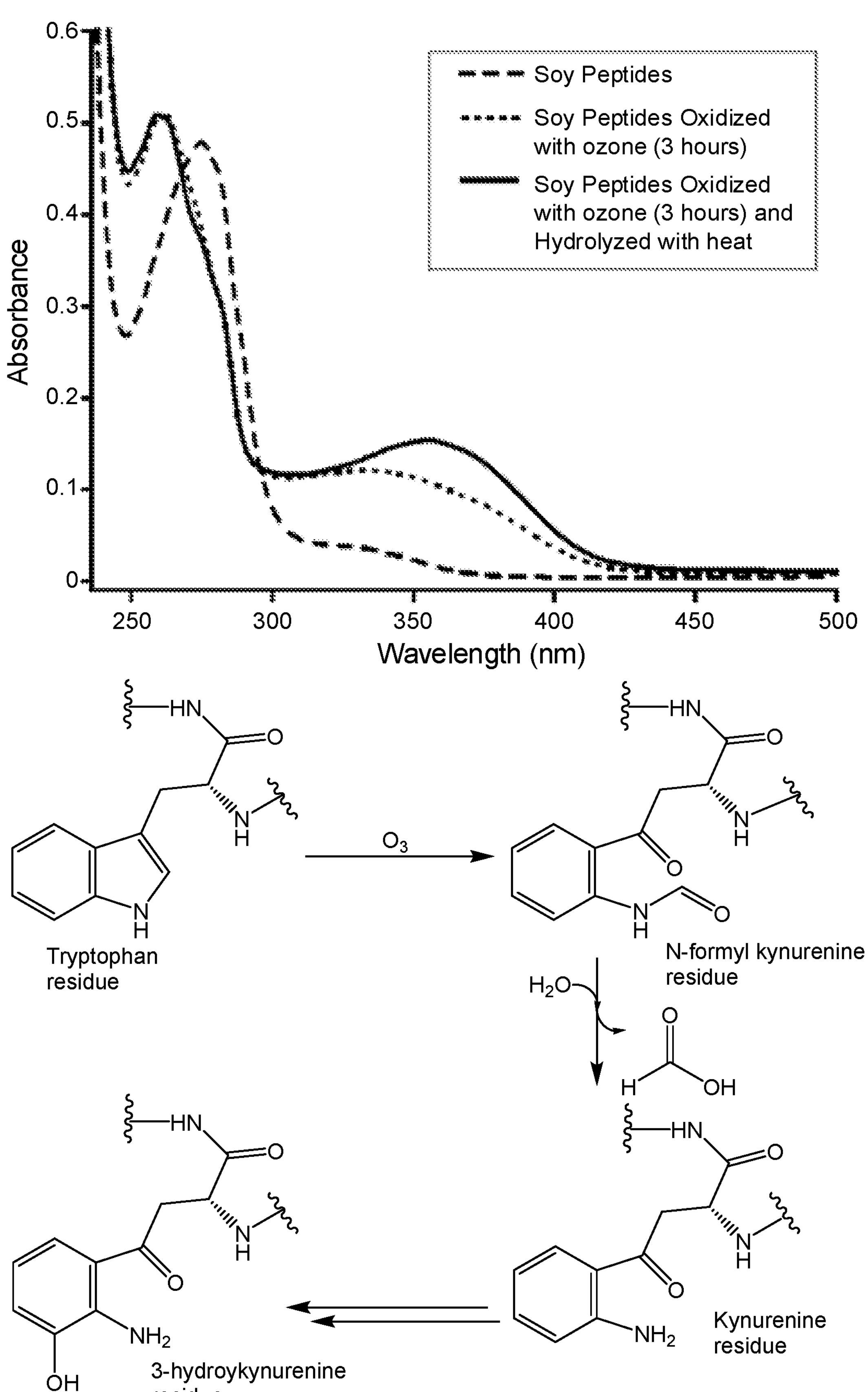
FIG. 3 is a line graph (top) showing the UV spectra of enzymatically hydrolyzed soy protein, the soy protein after ozonolysis, and the soy protein after ozonlysis and further hydrolysis (kynurenine hydrolysis product); and a scheme (bottom) showing the enzymatic hydrolysis of the soy protein and subsequent ozonolysis and hydrolysis.
Figure 4:
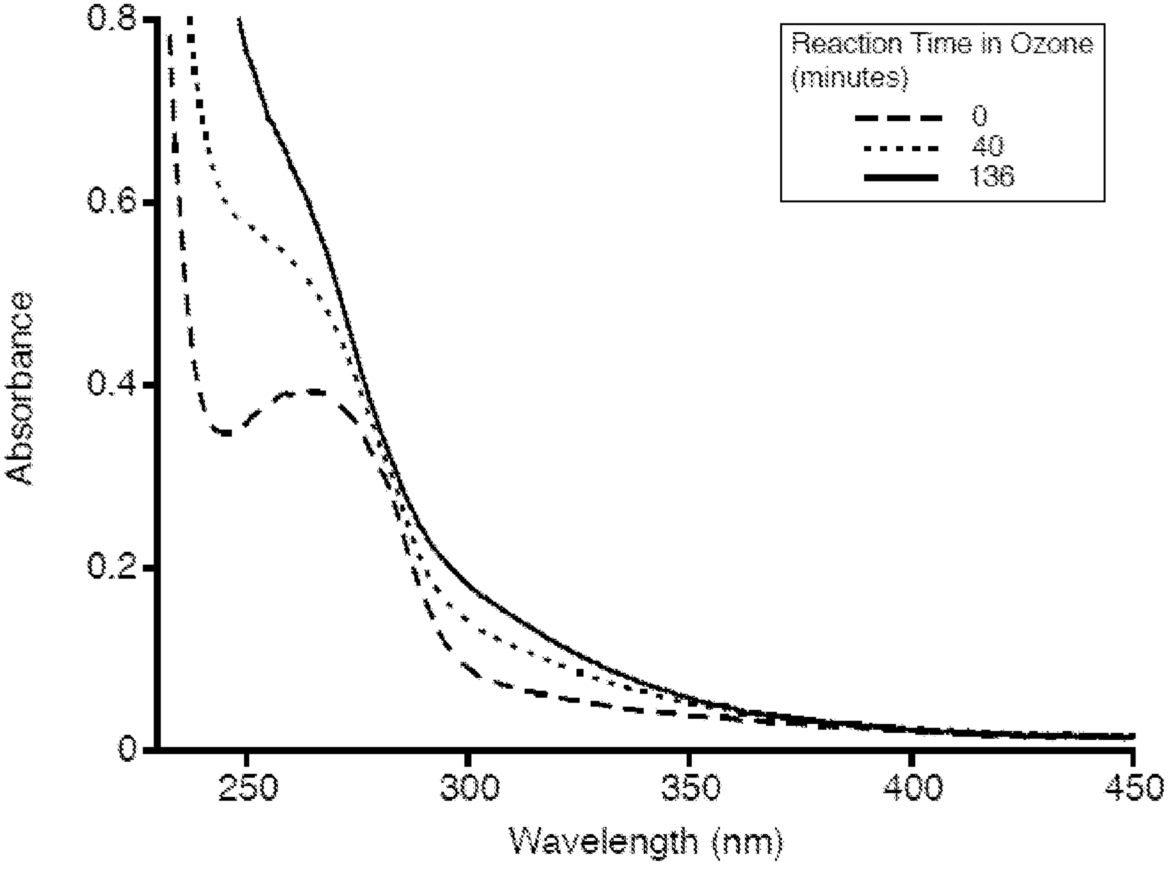
FIG. 4 is a line graph showing the UV spectra of pea protein peptone at various time points after exposure to ozone for 0, 40, and 136 minutes.

A prototype of kynurenine-bearing polymers was produced from enzymatic hydrolysis of soy protein generating starting peptide material. The soluble peptides were then oxidized in a semi-sealed container into which ozone was pumped. This produced oxidized products of the peptide-bound tryptophan, tyrosine, and phenylalanine residues. The formation of these products was monitored by UV-visible spectroscopy, which showed an increase in the absorbance at 300-350 nm, as shown in FIG. 3 (top), where the free amino acids of N-formyl kynurenine, dityrosine, O-linked dityrosine, and 3,4-dihydroxyphenylalnine absorb. The N-formyl kynurenine residues were then hydrolyzed by heating the peptide solution to 100° C. for 1 h, that contains the signature absorbance of kynurenine residues in the UVA (370 nm), as shown in FIG. 3 (top). Pea peptone was similarly oxidized with ozone to produce oxidized products of the peptide-bound tryptophan, tyrosine, and phenylalanine residues, resulting in increased absorbance from 300-350 nm, as shown in FIG. 4.

Example 4

Oxidation of Whole Proteins

Figure 5:
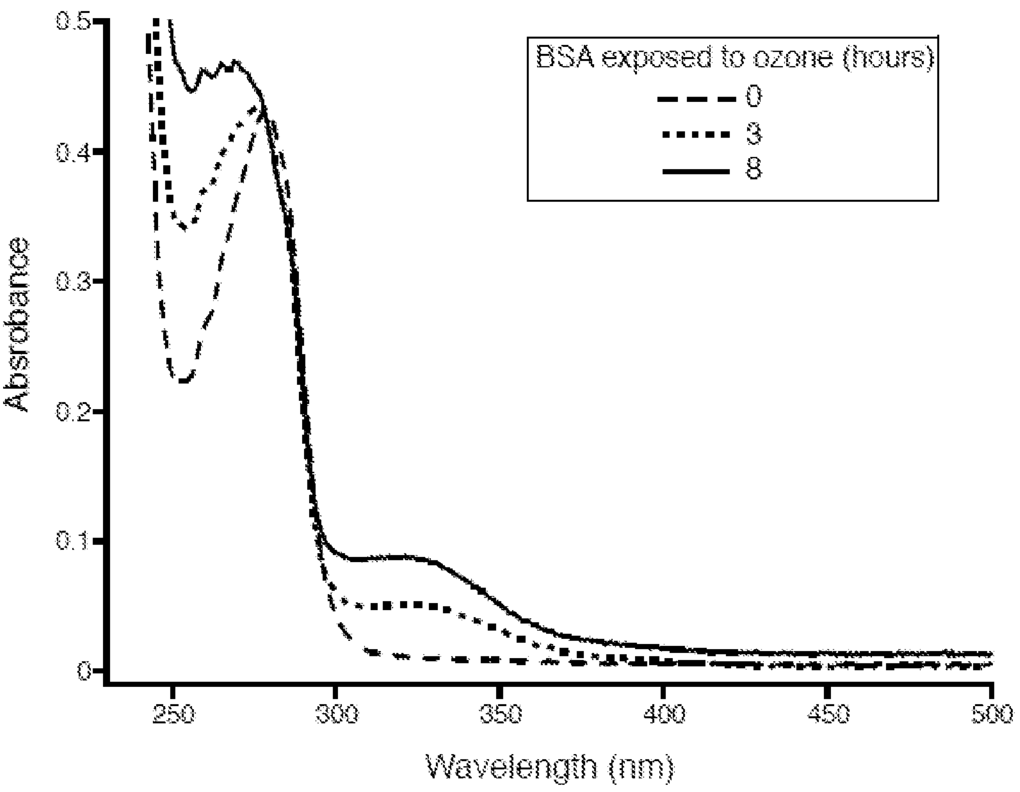
FIG. 5 is a line graph showing the UV spectra of bovine serum albumin after exposure to ozone for 0, 3, and 8 hours.

Whole proteins may also be used to generate macromolecules that possess UV-filtering residues, such as tryptophan residues converted to their N-formyl kynurenine and kynurenine derivatives. This was done with bovine serum albumin buffer exchanged with into 50 mM sodium phosphate pH 6.5 to remove small molecule impurities. The protein solution was then stirred under a stream of ozone from an ozone generator for 8 hours with samples taken at 0, 3, and 8 hours, as shown in FIG. 5. Over this period of time, a strong absorbance in the 300-350 nm region is produced, likely resulting mainly from tryptophan residues converting into their N-formyl kynurenine derivatives.

Example 5

Addition of Kynurenine Analogs to Polymers or Soy Peptides

Figure 6:
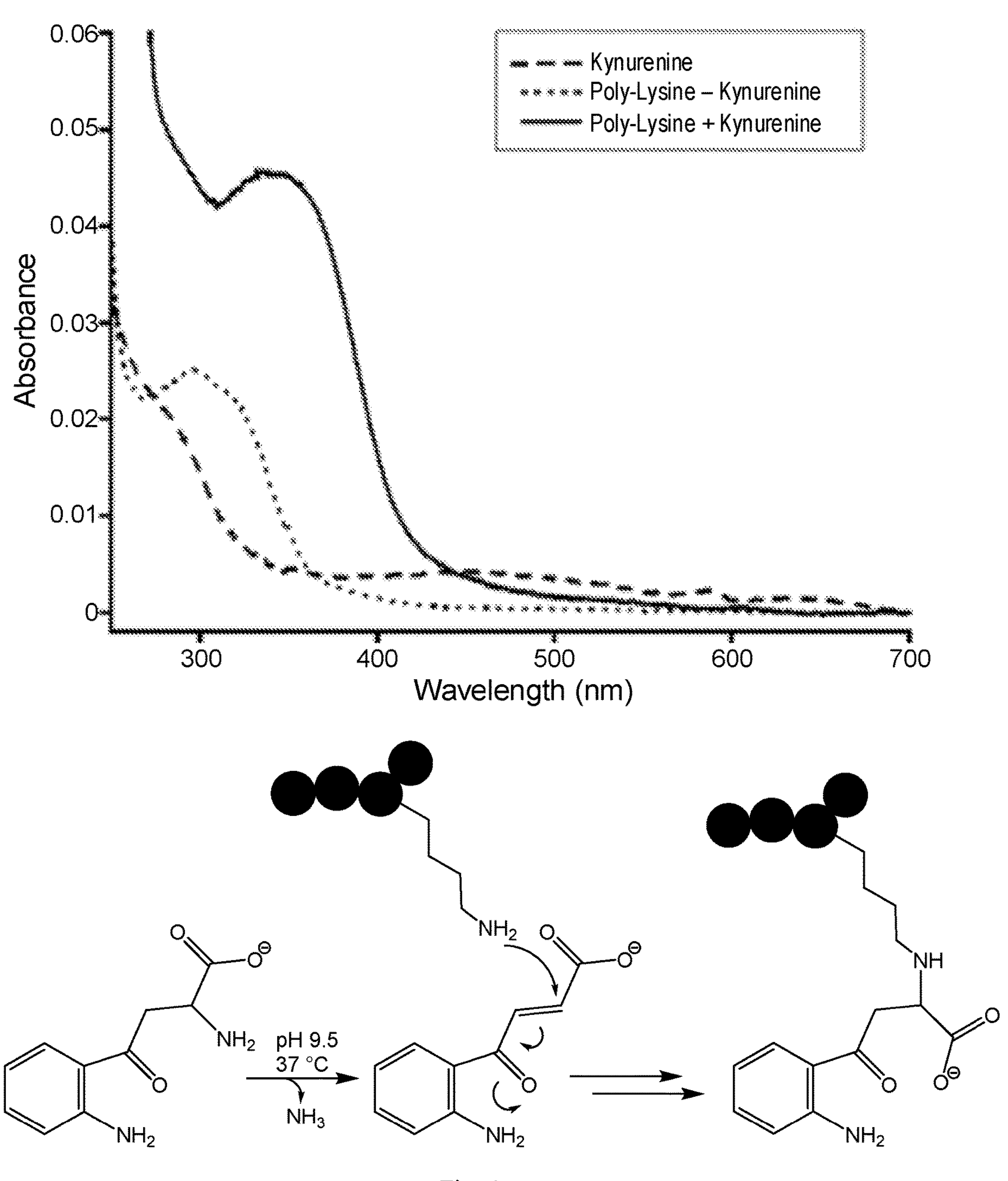
FIG. 6 is a line graph (top) showing the UV spectra of poly-lysine peptides before and after kynurenine analog addition, and kynurenine alone; and a scheme (bottom) depicting deamination of kynurenine to form the kynurenine analog (E)-4-(2-aminophenyl)-4-oxobut-2-enoic acid followed by nucleophilic addition of a poly-lysine amine group to the kynurenine analog.
Figure 7:
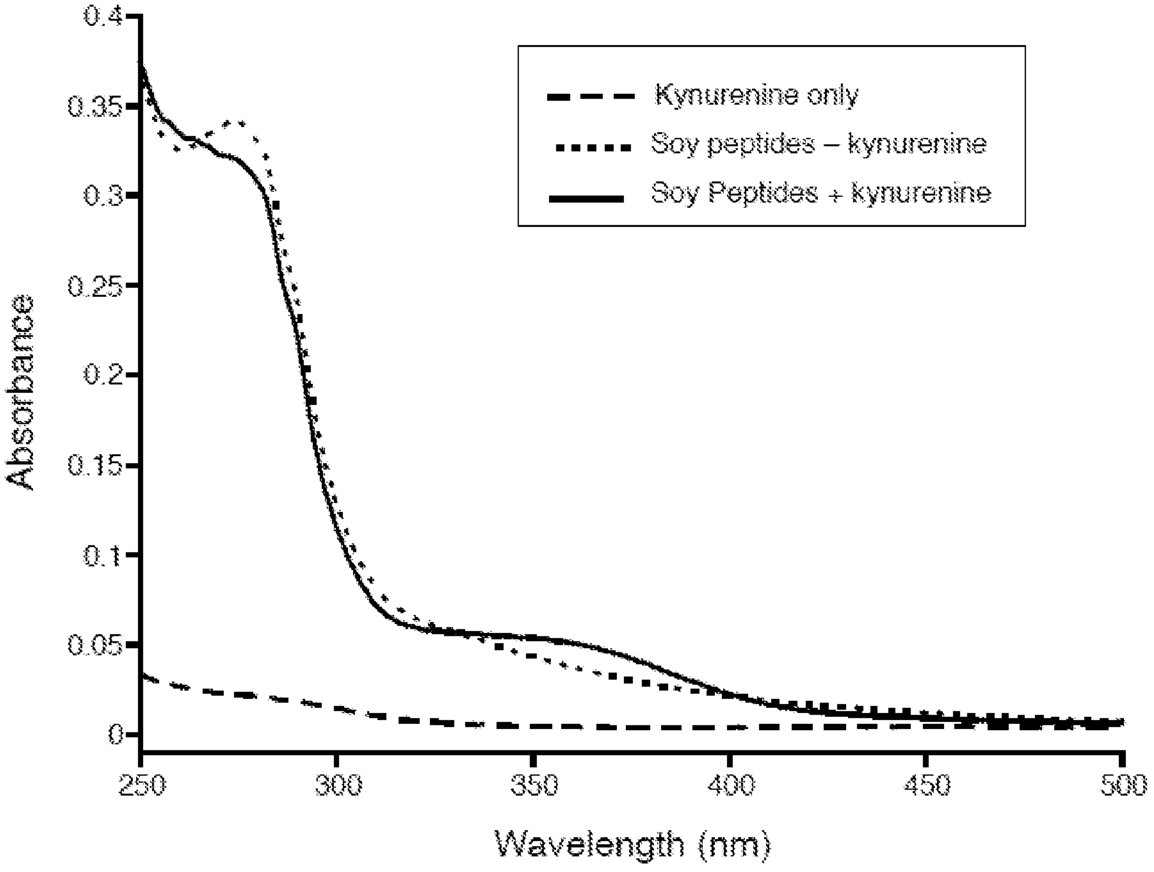
FIG. 7 is a line graph showing the UV spectra of soy peptides before and after kynurenine analog addition, and kynurenine alone.

To effect addition of kynurenine monomers to nucleophilic moities on polymers, a synthesis similar to that reported by Vasquez et al. was initiated using poly-L-lysine with molecular weight of 4,000 to 15,000 Da (Sigma P6516) or soy peptides. The polymeric lysine (8.8 mg) was suspended in 200 microliters of 50 mM sodium bicarbonate pH 9.5 and treated with DL-kynurenine (Sigma 61250) (~1 mM) for 44 hours at 37° C. in the dark. Because the added kynurenines lose the chiral center upon elimination of the alpha-amino group to form the reactive electrophilic alpha-beta unsaturated ketone, the chirality of the starting material does not matter. Controls of poly-lysine with no added kynurenine and that of kynurenine without poly-lysine were run concurrently. To remove excess kynurenine, the solutions were run over size exclusion columns (Sephadex G-50, GE Healthcare), and the resultant high molecular weight species showed increased absorbance in the 300-400 nm range, especially around 360 nm where kynurenine absorbs maximally in the UVA, as shown in FIG. 6. This only occurred with both poly-lysine and added kynurenine, indicating the expected addition of kynurenine monomers occurred. Soy peptides were used similarly, though they also contain other potential nucleophilic residues besides lysine to which kynurenine monomers could be added, including cysteine and histidine. These soy peptides were generated from overnight incubation at 37° C. of soy protein powder (5 g/100 mL deionized water) using porcine pepsin (0.5 mg/mL) all brought to pH 2.0 using hydrochloric acid. After this incubation, insoluble material was removed via centrifugation, and the clarified solution was brought to pH 9.5 using sodium hydroxide. This soy peptide solution was added in two parts to one part 50 mM sodium bicarbonate pH 9.5. To 1 mL of soy peptide solution was added 0.2 mL DLkynurenine (final 1 mM), and this was incubated for 44 hours at 37° C. in the dark. To isolate peptides from free kynurenine to determine if kynurenine monomers were added by UV-visible spectroscopy, small molecules and even some small peptides were removed with size exclusion (Sephadex G-50, GE Healthcare). The resulting solution showed an absorbance increase in the UVA region around 360 nm above that of peptides treated similarly but lacking added DL-kynurenine, showing that addition of kynurenine monomers to soy peptides had occurred, as shown in FIG. 7.

Example 6

Kynurenine Polymer UV Filters for Packaging

Figure 8:
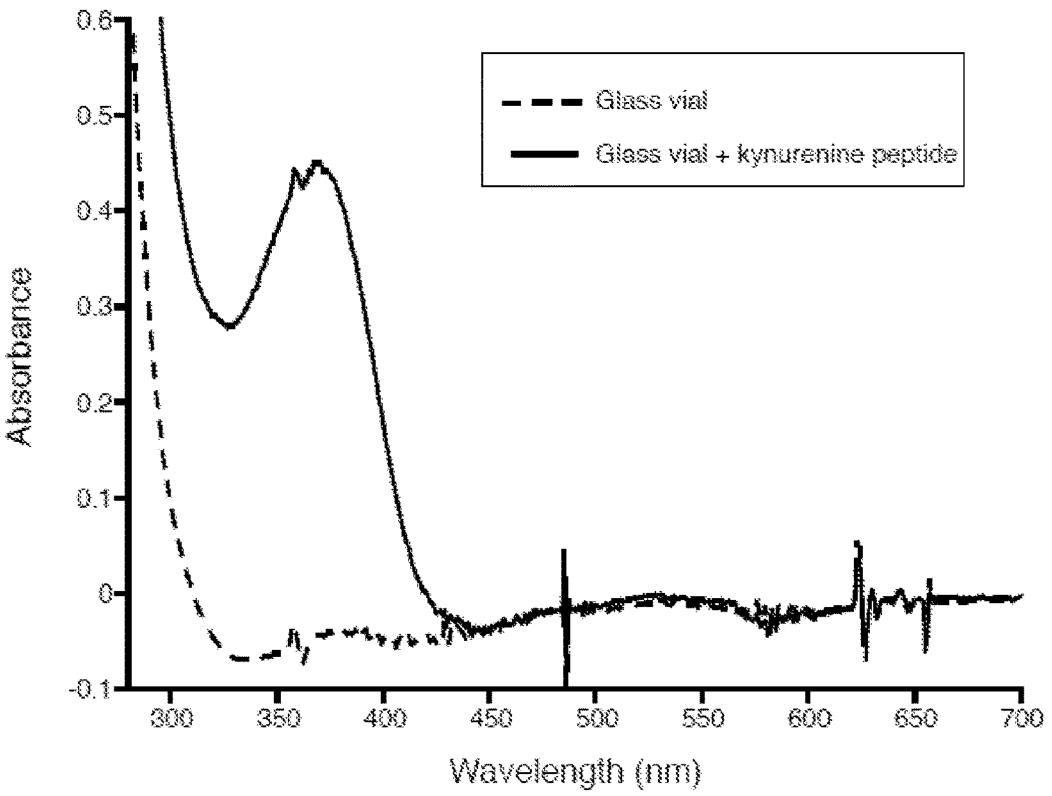
FIG. 8 is a line graph showing the UV spectra of a glass vial with or without soy peptides containing kynurenine residues.

Glass vials were coated with UV-filtering kynurenine-bound polymers and tested to show UV absorbance and protective qualities for light sensitive foods. To a 4 mL glass vial (Fisherbrand catalog number 03-391-19) was added polymer-bound kynurenine UV filters in the form of soy peptides that had been modified as in Example 3 above. The solution of peptides was reduced in volume under reduced pressure until it became more viscous almost like a syrup. Using a small paint brush, this solution was applied evenly to the glass vial and dried fully using a heat gun. The mass of the vial was measured before and after addition to show 9.2 mg dry weight of soy peptide kynurenine filter had been applied to a surface with an area of about 17 $cm^3$, giving 0.54 $mg/cm^3$ UV filter on the exterior of the vial. The characteristic absorption spectrum of kynurenine was seen on the glass with dried kynurenine peptide by placing it directly in the light path in a UV-visible spectrometer and comparing that to a similar glass vial without added kynurenine peptide filter, as shown in FIG. 8.

Figure 9:
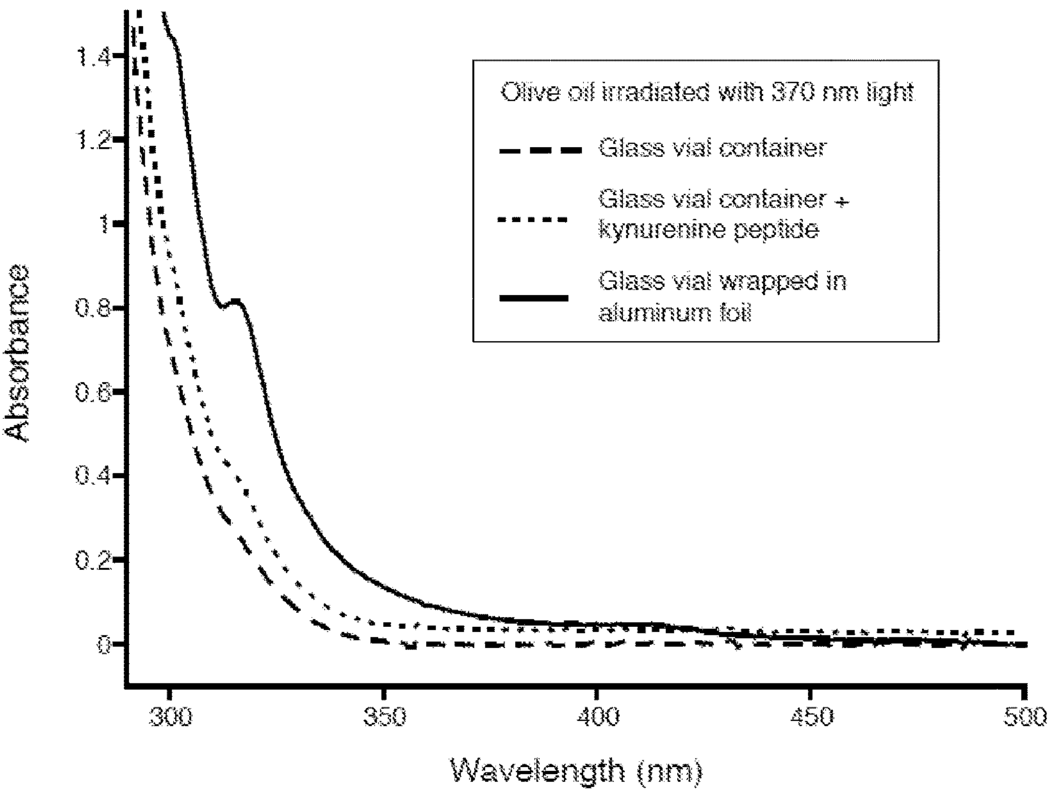
FIG. 9. is a line graph showing the UV spectra of olive oil after exposure to UV light while being stored in glass vials with an aluminum foil filter, a kynurenine soy peptide filter, and no filter.

This was tested for its UV-protective effects using olive oil that is sensitive to degradation under UVA light. For this, 2 mL of olive oil were added each to three vials, one with added kynurenine filter, one without, and one that was wrapped in aluminum foil to more fully block out light. These were left with lids open to air and subjected to 370 nm light using two 370 nm LED lamps (Kessil PR160-370 nm) each at about 3 inches away and set to full intensity. The kynurenine UV-filter fluoresced under this light with a slight blue-green color. After 24 hours the olive oil treated with 370 nm light was notably bleached compared to that protected with aluminum foil. The olive oil protected with the thin kynurenine peptide filter was bleached but to a lesser degree. This was quantified using the chromophore of olive oil at 315 nm for which each was sampled by taking 0.1 mL and diluting it with 0.5 mL hexane in a quartz cuvette. The kynurenine peptide filter protected the olive oil (Absorbance at 315 nm of 0.423) about 1.5× more than without added kynurenine peptide filter (Absorbance at 315 nm of 0.289) and about half of that completely protected from UV light by aluminum foil (Absorbance at 315 nm of 0.811), as shown in FIG. 9.

REFERENCES

1. Zhang, W.; Xiao, S.; Ahn, D. U., Protein oxidation: basic principles and implications for meat quality. Critical reviews in food science and nutrition 2013, 53 (11), 1191-1201.
2. Zhao, H.; Sagert, J.; Hwang, D. S.; Waite, J. H., Glycosylated hydroxytryptophan in a mussel adhesive protein from Perna viridis. Journal of Biological Chemistry 2009, 284 (35), 23344-23352.
3. Tsentalovich, Y. P.; Sherin, P. S.; Kopylova, L. V.; Cherepanov, I. V.; Grilj, J.; Vauthey, E., Photochemical properties of UV filter molecules of the human eye. Investigative ophthalmology & visual science 2011, 52 (10), 7687-7696.
4. Lesniak, W. G.; Jyoti, A.; Mishra, M. K.; Louissaint, N.; Romero, R.; Chugani, D. C.; Kannan, S.; Kannan, R. M., Concurrent quantification of tryptophan and its major metabolites. Analytical biochemistry 2013, 443 (2), 222-231.
5. Badawy, A. A., Kynurenine pathway of tryptophan metabolism: regulatory and functional aspects. International Journal of Tryptophan Research 2017, 10, 1178646917691938.
6. Ehrenshaft, M.; Deterding, L. J.; Mason, R. P., Tripping up Trp: Modification of protein tryptophan residues by reactive oxygen species, modes of detection, and biological consequences. Free Radical Biology and Medicine 2015, 89, 220-228.
7. Jensen, R. L.; Arnbjerg, J.; Ogilby, P. R., Reaction of singlet oxygen with tryptophan in proteins: a pronounced effect of the local environment on the reaction rate. Journal of the American Chemical Society 2012, 134 (23), 9820-9826.
8. Wong, C. T.; Lam, H. Y.; Li, X., Effective synthesis of kynurenine-containing peptides via on-resin ozonolysis of tryptophan residues: synthesis of cyclomontanin B. Organic & biomolecular chemistry 2013, 11 (43), 7616-7620.
9. Maskos, Z.; Rush, J.; Koppenol, W., The hydroxylation of tryptophan. Archives of biochemistry and biophysics 1992, 296 (2), 514-520.

10. Ogata, N., Denaturation of protein by chlorine dioxide: oxidative modification of tryptophan and tyrosine residues. Biochemistry 2007, 46 (16), 4898-4911.

11. Kato, Y.; Kawakishi, S.; Aoki, T.; Itakura, K.; Osawa, T., Oxidative modification of tryptophan residues exposed to peroxynitrite. Biochemical and biophysical research communications 1997, 234 (1), 82-84.

12. Roeser, J.; Permentier, H. P.; Bruins, A. P.; Bischoff, R., Electrochemical oxidation and cleavage of tyrosine- and tryptophan-containing tripeptides. Analytical chemistry 2010, 82 (18), 7556-7565.

13. Pattison, D. I.; Rahmanto, A. S.; Davies, M. J., Photo-oxidation of proteins. Photochemical & Photobiological Sciences 2012, 11 (1), 38-53.

14. Cataldo, F., On the action of ozone on proteins. Polymer Degradation and Stability 2003, 82 (1), 105-114.

15. Bos, J. D.; Meinardi, M. M., The 500 Dalton rule for the skin penetration of chemical compounds and drugs. Experimental Dermatology: Viewpoint 2000, 9 (3), 165-169.

16. Matta, M. K.; Florian, J.; Zusterzeel, R.; Pilli, N. R.; Patel, V.; Volpe, D. A.; Yang, Y.; Oh, L.; Bashaw, E.; Zineh, I., Effect of sunscreen application on plasma concentration of sunscreen active ingredients: a randomized clinical trial. Jama 2020, 323 (3), 256-267.

17. Danovaro, R.; Bongiorni, L.; Corinaldesi, C.; Giovannelli, D.; Damiani, E.; Astolfi, P.; Greci, L.; Pusceddu, A., Sunscreens cause coral bleaching by promoting viral infections. Environmental health perspectives 2008, 116 (4), 441-447.

18. Diaz-Cruz, M. S.; Barceló, D., Chemical analysis and ecotoxicological effects of organic UV-absorbing compounds in aquatic ecosystems. TrAC Trends in Analytical Chemistry 2009, 28 (6), 708-717.

19. Sánchez-Quiles, D.; Tovar-Sánchez, A., Sunscreens as a source of hydrogen peroxide production in coastal waters. Environmental science & technology 2014, 48 (16), 9037-9042.

20. Miller, R. J.; Bennett, S.; Keller, A. A.; Pease, S.; Lenihan, H. S., TiO 2 nanoparticles are phototoxic to marine phytoplankton. PloS one 2012, 7 (1), e30321.

21. Hanson, K. M.; Gratton, E.; Bardeen, C. J., Sunscreen enhancement of UV-induced reactive oxygen species in the skin. Free Radical Biology and Medicine 2006, 41 (8), 1205-1212.

22. Ogilby, P. R., Singlet oxygen: there is indeed something new under the sun. Chemical Society Reviews 2010, 39 (8), 3181-3209.

23. Bohling, A.; Bielfeldt, S.; Himmelmann, A.; Keskin, M.; Wilhelm, K. P., Comparison of the stratum corneum thickness measured in vivo with confocal Raman spectroscopy and confocal reflectance microscopy. Skin Research and Technology 2014, 20 (1), 50-57.

24. Secchi, G., Role of protein in cosmetics. Clinics in dermatology 2008, 26 (4), 321-325.

25. Wang, H.; Wu, Y.; O'Brien, J., Method for identifying skin care composition-resistant skin-binding peptides. Google Patents: 2006.

26. Lowe, D. J.; O'brien, J. P.; Wilkins, A. E., Peptide-based organic sunscreens. Google Patents: 2012.

27. Anton, D. R.; Daly, S.; Bianchini, R. J.; Wang, H.; Rouviere, P. E.; Cunningham, S. D.; Fahnestock, S. R.; Gruber, T. M., Peptide-based systems for delivery of cosmetic agents. Google Patents: 2010.

28. Mezrich, J. D.; Fechner, J. H.; Zhang, X.; Johnson, B. P.; Burlingham, W. J.; Bradfield, C. A., An interaction between kynurenine and the aryl hydrocarbon receptor can generate regulatory T cells. The Journal of Immunology 2010, 185 (6), 3190-3198.

29. Günther, J.; Fallarino, F.; Fuchs, D.; Wirthgen, E., Immunomodulatory roles of tryptophan metabolites in inflammation and cancer. Frontiers in Immunology 2020, 11, 1497.

30. Belsito, D. V.; Hill, R. A.; Klaassen, C. D.; Liebler, D. C.; Marks Jr, J. G.; Shank, R. C.; Slaga, T. J.; Snyder, P. W., Safety Assessment of Plant-Derived Proteins and Peptides as Used in Cosmetics. 2017.

31. Davies, M. J., Protein oxidation and peroxidation. Biochemical Journal 2016, 473 (7), 805-825.

32. Jocelyn, P. C., Chemical reduction of disulfides. Methods in enzymology 1987, 143, 246-256.

33. Mudd, J.; Leavitt, R.; Ongun, A.; McManus, T., Reaction of ozone with amino acids and proteins. Atmospheric Environment (1967) 1969, 3 (6), 669-681.

34. EP1038516A1 (Cosmetic composition comprising kynurenine): this patent describes free kynurenine, not kynurenine derived from and/or bound to a polymer.

35. U.S. Pat. No. 8,318,659B2 (Peptide-Based Organic Sunscreens): this patent does not specify kynurenine, it entails a general organic sunscreen attached at the end of a peptide, and it does not entail the conversion of genetically encoded peptide-bound tryptophan residues into their naturally occurring kynurenine derivatives.

36. Vazquez, S.; Aquilina, J. A.; Sheil, M. M.; Truscott, R. J.; Jamie, J. F., Novel protein modification by kynurenine in human lenses. *Journal of Biological Chemistry* 2002, 277 (7), 4867-4873.

Further description of the disclosed composition of matter, systems, and products are included in the Appendix which are part of the application and is incorporated by reference in its entirety as if fully set forth herein. The Appendix comprises two documents describing the addition of kynurenine and its analogs to peptides and polymers. In addition, the references listed herein are also part of the application and are incorporated by reference in their entirety as if fully set forth herein.

What is claimed is:

1. A composition of matter comprising a polymer or peptide bound to an oxidized amino acid.

2. The composition of matter of claim 1, wherein the oxidized amino acid is an oxidation product of an amino acid selected from the group consisting of tryptophan, tyrosine, phenylalanine, methionine, cysteine, and histidine.

3. The composition of matter of claim 1, wherein the oxidized amino acid is a kynurenine.

4. The composition of matter of claim 1, wherein the polymer or peptide and oxidized amino acid together have a molecular weight of from about 100 Da to about 100,000 Da.

5. The composition of matter of claim 1, wherein the polymer or peptide and oxidized amino acid together have a molecular weight of from about 100 Da to about 1,000 Da.

6. The composition of matter of claim 1, wherein the polymer is a poly (meth) acrylate, a polymethyl (meth) acrylate, a polyamide, a polyurethane, a polyvinylacrylate, a polyester, a poly (meth) acrylic acid ester, a polyvinylester, a polylactic acid ester, a polyhydroxyalkanoate, polyhydroxybutyrate, polyhydroxybutyric acid, or copolymers thereof or combinations thereof.

7. The composition of matter of claim 1 wherein the composition of matter comprises an amide bond between an amine of the polymer and a carboxylate of kynurenine.

8. The composition of matter of claim 1 wherein the composition of matter comprises an amide bond between a carboxylic acid of the polymer and an amine of kynurenine.

9. The composition of matter of claim 1, wherein the composition is comprised in a sunscreen that provides UV-A and UV-B protection.

10. The composition of matter of claim 1, wherein the composition of matter has a form of a lotion, light ointment, oil, gel, emulsion, mousse, aerosol, stick, or powder.

11. The composition of matter of claim 1, wherein the composition of matter provides UVB protection and UVA protection from about 350 nm to about 370 nm.

12. The composition of matter of claim 1, further comprising one or more of an oil component, a moisturizing agent, a surfactant, and a carrier.

13. The composition of matter of claim 12, wherein the carrier is a water-in-oil emulsion, an oil, an aqueous-based lotion or gel, or an anhydrous gel.

14. The composition of matter of claim 1, wherein the composition of matter comprises from about 0.1 wt % to about 25 wt % of the polymer or peptide bound to an oxidized amino acid.

15. The composition of matter of claim 1, further comprising one or more thickening agents, film forming agents, surfactants, skin conditioning agents, or a combination thereof.

* * * * *